United States Patent [19]
Wedeen

[11] Patent Number: 4,752,734
[45] Date of Patent: Jun. 21, 1988

[54] FLOW IMAGING BY MEANS OF NUCLEAR MAGNETIC RESONANCE

[75] Inventor: Van J. Wedeen, Cambridge, Mass.

[73] Assignee: The General Hospital Corporation, Boston, Mass.

[21] Appl. No.: 18,847

[22] Filed: Feb. 24, 1987

Related U.S. Application Data

[63] Continuation of Ser. No. 763,096, Aug. 6, 1985, abandoned, which is a continuation-in-part of Ser. No. 640,040, Aug. 10, 1984, Pat. No. 4,625,169.

[51] Int. Cl.$^4$ ............................................. G01R 33/20
[52] U.S. Cl. .................................... 324/306; 324/309
[58] Field of Search ................ 128/653; 324/300, 306, 324/307, 309

[56] References Cited

U.S. PATENT DOCUMENTS

| | | | |
|---|---|---|---|
| 3,562,632 | 2/1971 | Kirkland | 324/0.5 |
| 4,110,680 | 8/1978 | Bergmann et al. | 324/0.5 |
| 4,442,404 | 4/1984 | Bergmann | 324/309 |
| 4,523,596 | 6/1985 | Macovski | 128/653 |
| 4,574,240 | 3/1986 | Libove et al. | 324/309 |
| 4,609,872 | 9/1986 | O'Donnell | 324/309 |

FOREIGN PATENT DOCUMENTS

| | | |
|---|---|---|
| 115641 | 8/1984 | European Pat. Off. . |
| 117134 | 8/1984 | European Pat. Off. . |
| 2127155 | 4/1984 | United Kingdom . |

OTHER PUBLICATIONS

Moran, "A Flow Velocity Zeugmatographic Interlace for NMR Imaging in Humans", *Magnetic Resonance Imaging*, vol. I, pp. 197–203, 1982.
Macovski, "Selective Projection Imaging: Applications to Radiography and NMR", IEEE Transactions on Medical Imaging, vol. MI-1, No. 1, Jul. 1982.
Carr et al., "Effects of Diffusion on Free Precession in Nuclear Magnetic Resonance Experiments", *Physical Review*, vol. 94, No. 3, pp. 630–638.
van Dijk, "Direct Cardiac NMR Imaging of Heart Wall and Blood Flow Velocity", *Journal of Computer Assisted Tomography*, 8(3), Jun. 1984.
Mills et al. "Nuclear Magnetic Resonance: Principles of Blood Flow Imaging", *American Journal of Neuroradiology*, Nov./Dec. 1983, pp. 1161–1166.
Singer, "NMR Diffusion and Flow Measurements and an Introduction to Spin Phase Graphing", *Journal of Physics E, Scientific Instruments*, Apr. 1978, vol. 11, No. 4, pp. 281–291.
Moran et al., "Verification and Evaluation of Internal Flow and Motion", *Radiology*, Feb. 1985, vol. 154, No. 2, 433–440.
Perman et al., Abstract, "Projection Flow Imaging", Scientific Program, vol. 153(P), Nov. 25, 1984.
Lent et al., Abstract, "Flow–Velocity Imaging by NMR", Scientific Program, vol. 149(P), Nov. 14, 1983.
Waluch et al., "NMR Even Echo Rephasing in Slow Laminar Flow", *Journal of Computer Assisted Tomography*, 8(4), Aug. 1984, pp. 594–598.
Singer et al., "Nuclear Magnetic Resonance Blood Flow Measurements in the Human Brain", *Science*, Aug. 1983, vol. 221, No. 4610, pp. 654–656.

*Primary Examiner*—Michael J. Tokar

[57] ABSTRACT

A nuclear magnetic resonance projection image of fluid flow in a vessel is obtained by generating two data sets encoded with phase information indicative of two different velocity profiles of the fluid (taken at different times), combining the data sets, and displaying the resulting data set as an image.

19 Claims, 28 Drawing Sheets

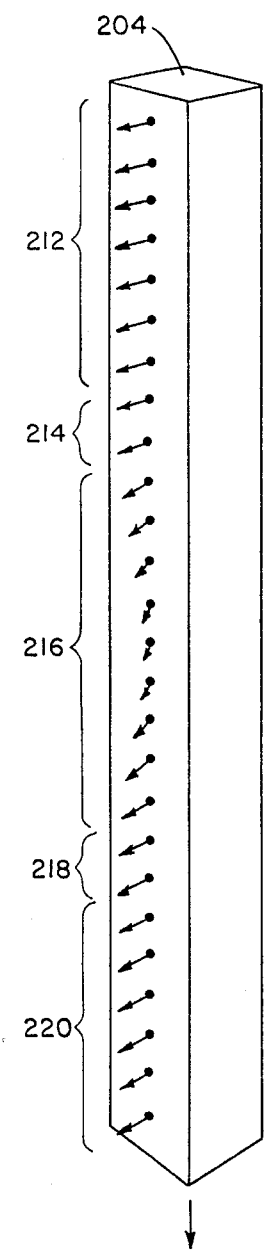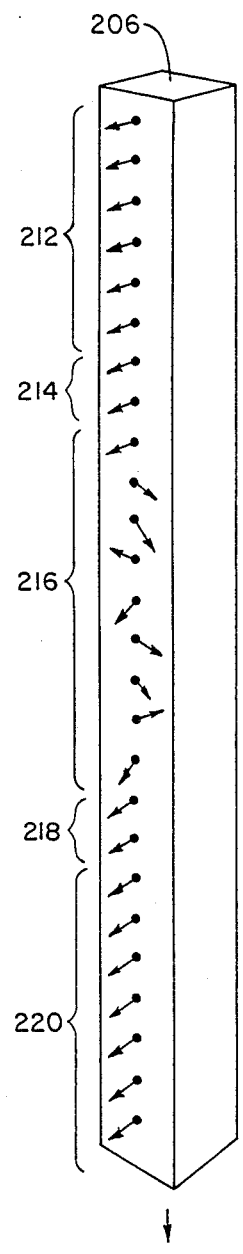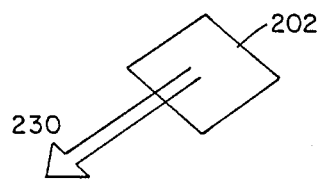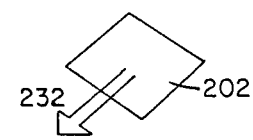
FIG 15                    FIG 16

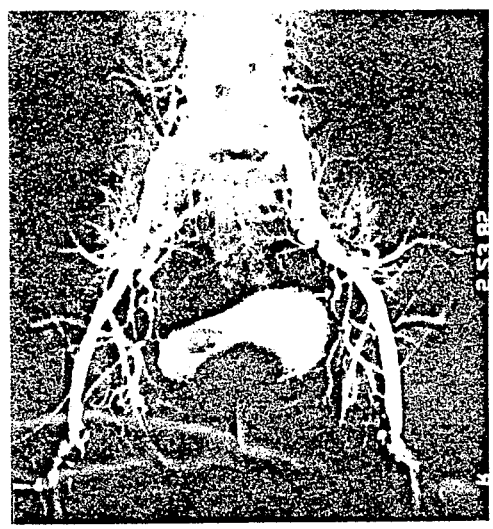
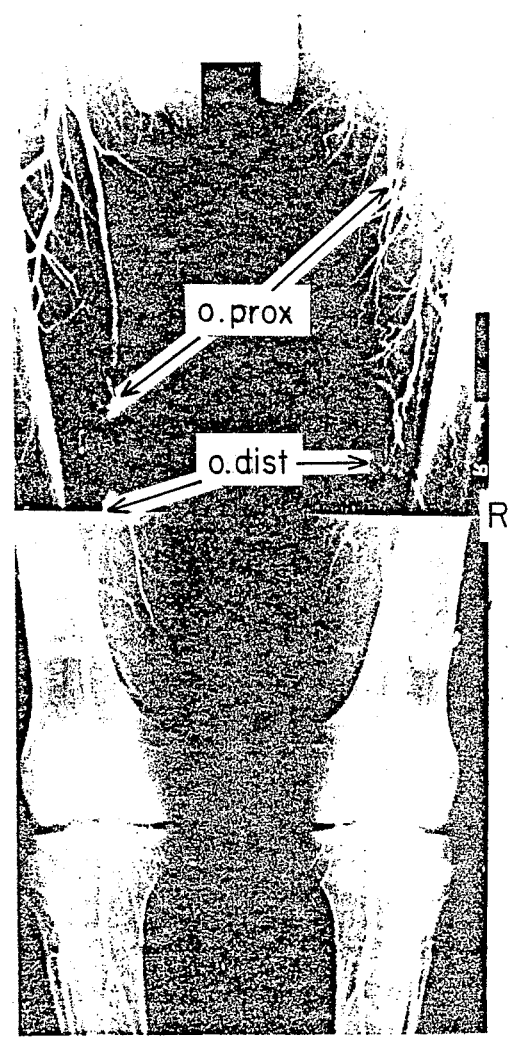
FIG 24

FLOW IMAGING BY MEANS OF NUCLEAR MAGNETIC RESONANCE

BACKGROUND OF THE INVENTION

This is a continuation of co-pending application Ser. No. 763,096 filed on Aug. 6, 1985, now abandoned which application is a continuation-in-part of U.S. patent application Ser. No. 640,040, filed Aug. 10, 1984 now U.S. Pat. No. 4,625,169, and assigned to the same assignee as this application.

This invention relates to nuclear magnetic resonance (NMR) imaging.

NMR imaging techniques can be used to form a picture of a cross-section of a three-dimensional object (for example, a human organ) in which its structure is indicated by variations in intensity or color of the picture.

One common technique for forming such an image uses a first magnetic field pulse having a linear gradient along a z-axis ($G_z$) to select the "slice" corresponding to the desired cross-section, a second pulse (called a phase-encoding pulse) having a linear gradient along the y-axis ($G_y$) to encode nuclei at different y-axis positions with different precessional phases, and a third linear gradient pulse (called a frequency-encoding pulse) along the x-axis ($G_x$) to encode nuclei at different x-axis positions with different frequencies. An appropriately modulated RF signal generator imposes a 90° RF pulse followed (after an appropriate interval) by a 180° pulse. The resulting time-dependent resonance spin-echo signal is measured and stored. The process is repeated to obtain a family of spin-echo signals each based upon a different magnitude of phase-encoding gradient $G_y$. The family represents a two-dimensional array of time-dependent information. A two-dimensional Fourier transformation of the spin-echo signal array produces a two-dimensional array of frequency-domain data which can be displayed as an image of the selected slice.

In addition to such images of the structure of organs, it has been suggested that NMR techniques be used in analyzing flow characteristics. For example, information about the flow of blood in an artery could be useful in analyzing deformities of the wall of the artery.

Moran, "A Flow Velocity Zeugmatographic Interlace for NMR Imaging in Humans", Magnetic Resonance Imaging, 1983, discloses adding to the usual imaging gradients, a special sequence of gradient pulses (for example, along the z-axis) to encode the nuclei with information about their velocity which can then be recaptured by Fourier transformation. The special gradient pulses are arranged to eliminate any dependence of the velocity-encoded information on spatial location. The article suggests using the imaginary component of the resulting data as an image of flow-current-density, and the ratios of the real to imaginary components of the data as an image of specific-flow-density.

In addition to cross-sectional images, NMR techniques have been used to produce three-dimensional projection images in which the data for a stack of cross-sectional slices are effectively added together. Macovski, "Selective Projective Imaging: Applications to Radiography and NMR," IEEE Transactions on Medical Imaging, Vol. MI-1, No. 1, pp. 42–44, July, 1982, discloses selective projective imaging in which subtraction of unwanted image components is proposed to be used in displaying moving blood without displaying the surrounding tissue. In particular, Macovski proposes to use a temporal subtraction approach in which data would be acquired at two different portions of the heart cycle corresponding to different velocities in the vessel and the data would be subtracted in order to cancel all static material and visualize the vessels.

Carr, H. Y., and Purcell, E. M., 1954 Phys. Rev. 94, p. 630, recognized that the motion of nuclei in a magnetic gradient will modify their phases in a way which is reflected in a shift in phase at the center of the spin echo.

SUMMARY OF THE INVENTION

The general feature of the invention is in forming an image representative of fluid flow in a vessel situated within a matrix (where the fluid flows with a first velocity profile at a first time and with a second velocity profile, different from the first velocity profile, at a second time) by stimulating the fluid, vessel, and matrix to produce a time-dependent magnetic resonance signal; producing data from the signal; introducing into the data phase information indicative of the velocity of the fluid as of a given time; extracting the phase information as a data set representative of a projection image of the fluid, vessel, and matrix as of that given time; generating two such data sets corresponding to two projection images respectively as of the first and second times corresponding to the first and second velocity profiles; combining the data sets to form a resulting data set; and displaying the resulting data set as the image representative of the fluid flow in the vessel.

Preferred embodiments of the invention include the following features. A sequence of RF and magnetic gradient pulses is imparted to the fluid, vessel, and matrix beginning at a predetermined time to produce the resonance signal, and the sequences used to generate the two data sets are identical. The first velocity profile includes a first range of velocities, the second velocity profile includes a second range of velocities higher than the first range, and phases are imparted to protons in the fluid with respect to the first velocity profile that are within a predetermined angle of the phases imparted to protons in the vessel and matrix, and random phases are imparted to protons in the fluid with respect to the second velocity profile. The phase shifts are imparted in protons in the fluid at a rate of $2\pi$ radians for a predetermined velocity level of the fluid that is higher than the first range of velocities and lower than the second range of velocities. The fluid is blood, the first range of velocities are the velocities of blood flowing in diastole, and the second range of velocities are the velocities of blood flowing in systole. The first data set is based on the occurrence of diastole (e.g., follows a QRS complex by 10 milliseconds), and the second time follows diastole by a predetermined interval (between 100 and 300 milliseconds after QRS complex) based on the location of the vessel relative to the heart. The pulse sequence is a two-dimensional Fourier transform spin echo pulse sequence, that includes 90° and 180° RF pulses, and a pair of magnetic gradient pulses along an axis of the vessel, the gradient pulses comprising a compensating pulse preceding the 180° RF pulse and a readout pulse following the 180° RF pulse, the two magnetic gradient pulses being of magnitudes and durations such that for static protons the phase shift imposed by one gradient pulse is exactly canceled by the phase shift imposed by the other gradient pulse. The spin echo occurs no later than 15 milliseconds after the 90° RF pulse. The vessel is an artery. The matrix is a tissue. The fluid flow is pulsatile. The data produced from the resonance signal is Fourier transformed data.

The resulting projection image has high contrast and high resolution. The vascular system is shown in detail while the static matrix is suppressed.

The projection images are easily obtained without requiring special velocity-encoding gradient pulses in addition to the phase-encoding and frequency-encoding pulses. The images are produced from the readily available real component of the Fourier-transformed data.

Other advantages and features of the invention will become apparent from the following description of the preferred embodiment, and from the claims.

DESCRIPTION OF THE PREFERRED EMBODIMENT

We first briefly describe the drawings.

DRAWINGS

FIGS. 15, 16 are isometric diagrams of the proton phases in diastole and systole voxels.

FIGS. 17 through 23, 25, and 26 are projection images of human subjects.

Figure 25:
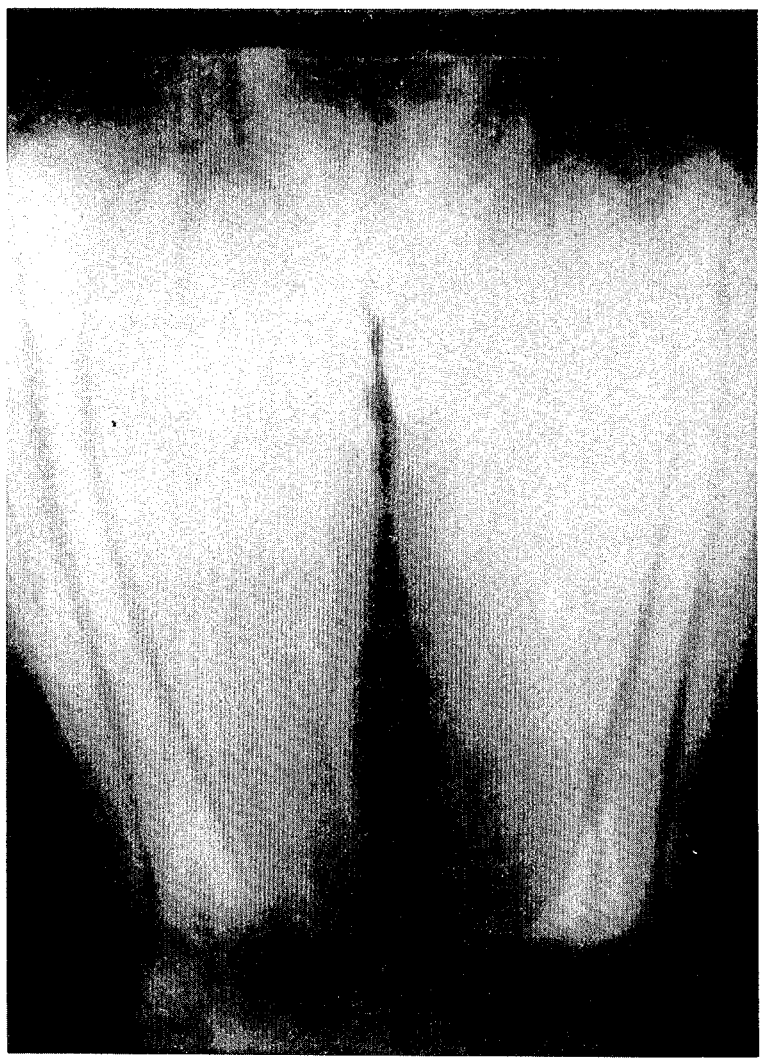
Figure 26:
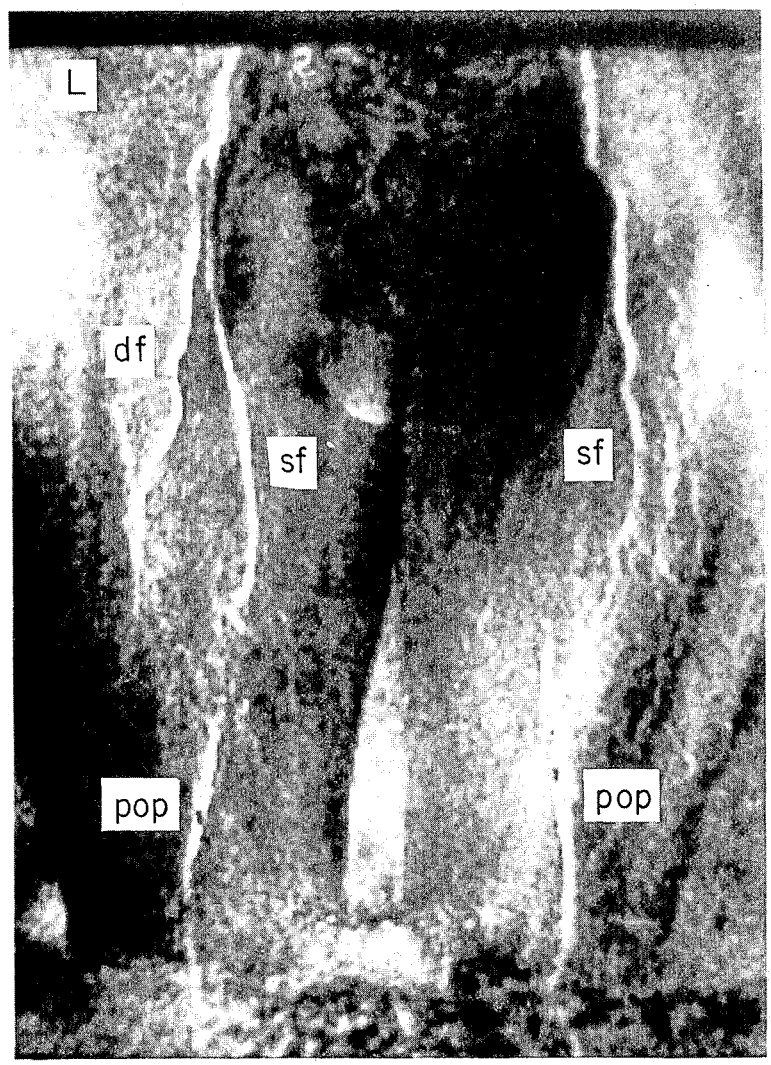

FIG. 24 is an x-ray image corresponding to FIGS. 25, 26.

Figure 3:
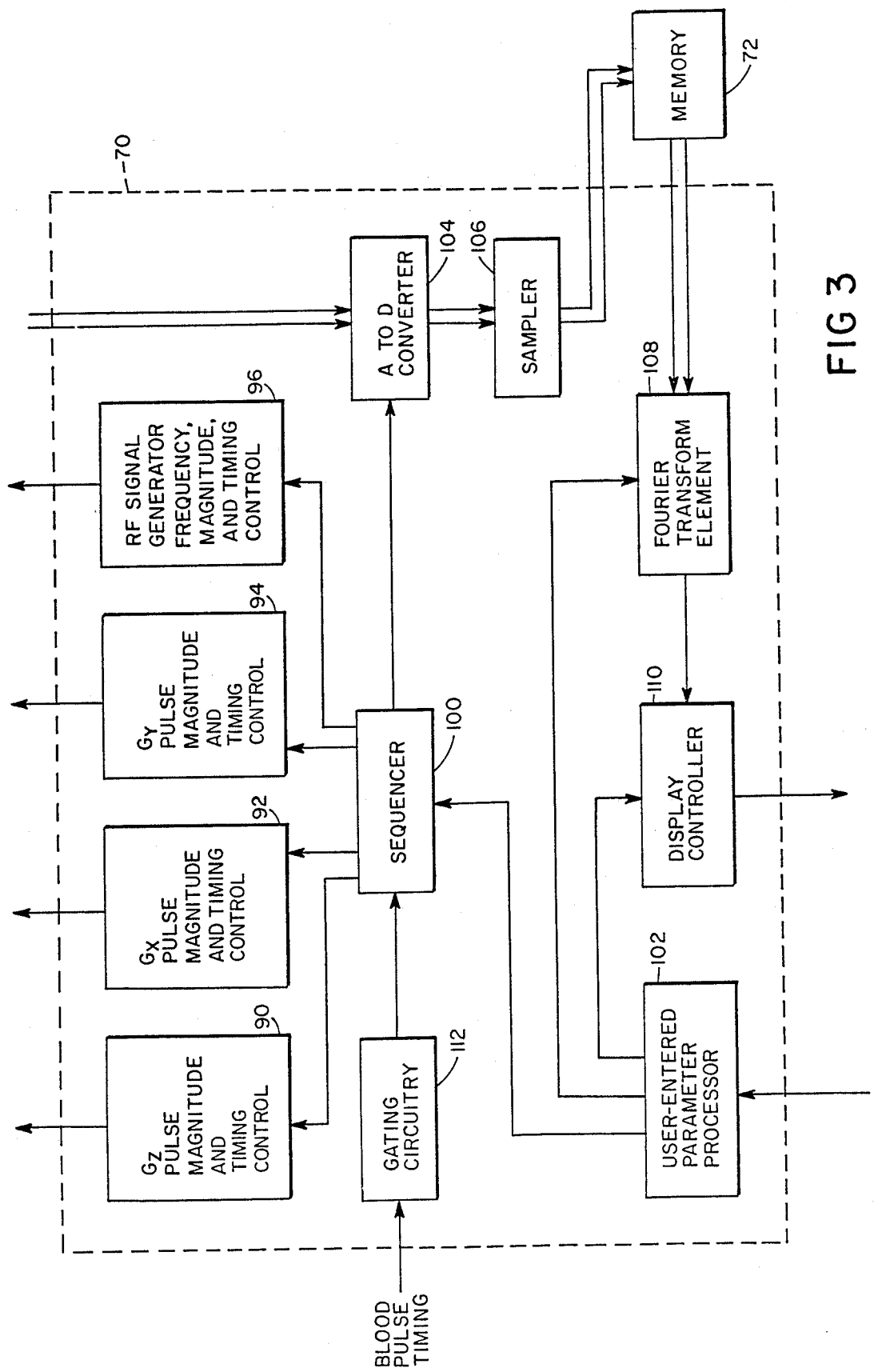
FIG. 3 is a block diagram of portions of the computer processor of FIG. 2.
Figure 27:
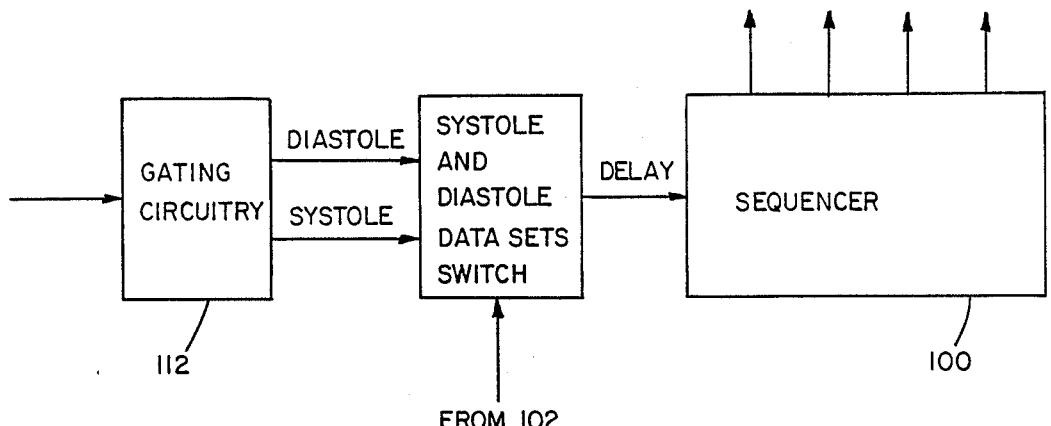
Figure 28:
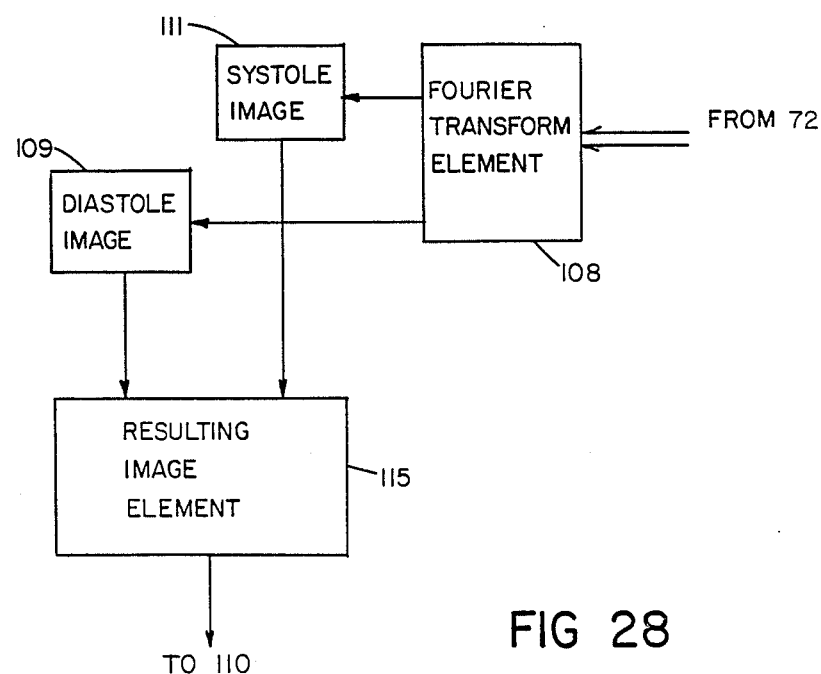

FIGS. 27, 28 show block diagrams of portions of the structure of FIG. 3.

STRUCTURE

Figure 1:
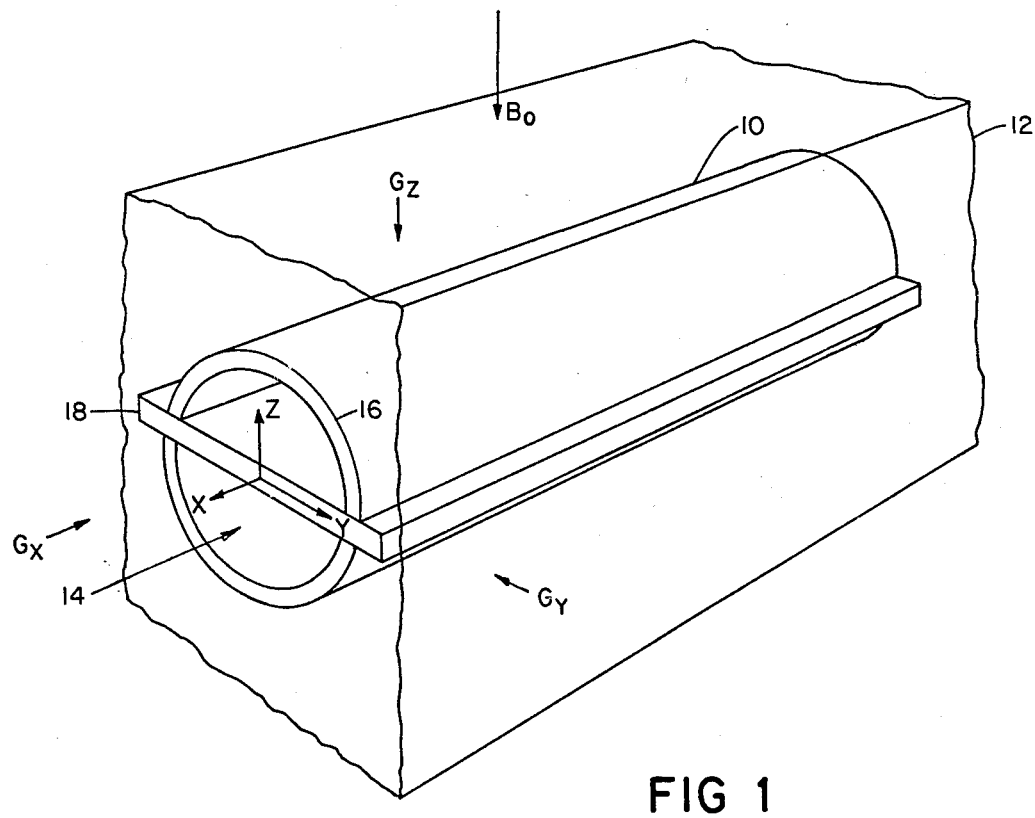
FIG. 1 is an isometric view of a short segment of a blood vessel and surrounding tissue.

Referring to FIG. 1, blood vessel 10 lies within a matrix of tissue 12 and carries blood flowing in the direction indicated by arrow 14. The velocity of the blood in direction tends to vary depending on how close it is to wall 16 of vessel 10. For example, in certain types of laminar flow the velocity of the blood is smallest at wall 16 and increases to a maximum at the central axis x of vessel 10. Thus, for a particular imaginary planar slice 18 (having a particular location along axis z) the blood velocity component in the x direction might vary from small to large to small as one traverses the slice from one wall to the opposite wall in a direction indicated by axis y.

Figure 2:
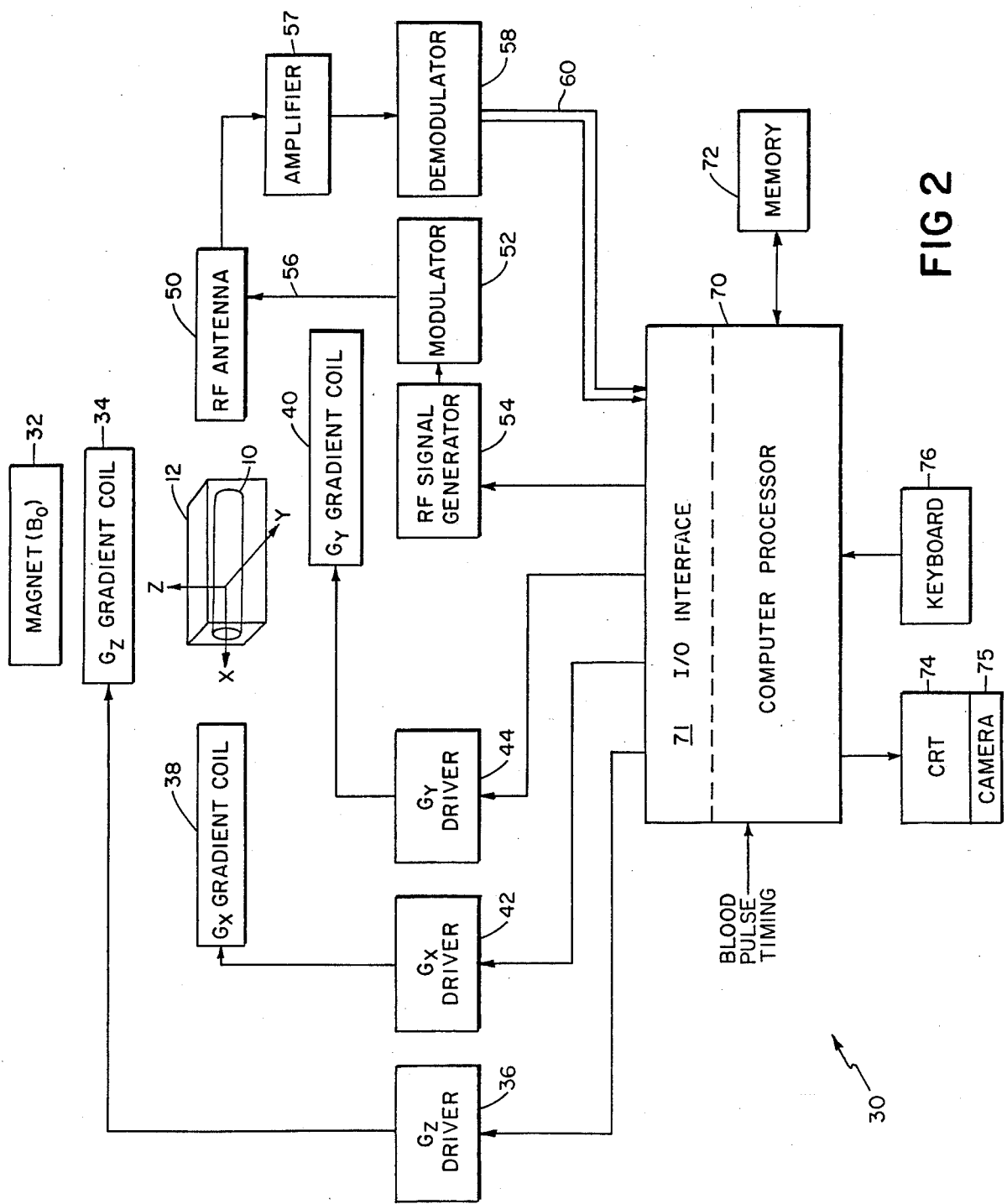
FIG. 2 is a block diagram of NMR apparatus.

Referring to FIG. 2, nuclear magnetic resonance apparatus 30 has a magnet 32 for imposing a uniform constant magnetic field $B_o$ on vessel 10 and tissue 12. A $G_z$ gradient coil 34 (arranged to provide a linear magnetic field gradient along the z-axis) is connected to a $G_z$ driver 36, which can provide selected levels of power at selected times to coil 34. Likewise, $G_x$ gradient coil 38 and $G_y$ gradient coil 40, which can provide linear magnetic field gradients respectively along the x-axis and y-axis, are respectively connected to $G_x$ driver 42 and $G_y$ driver 44, for providing power to the coils.

An RF antenna 50 (arranged to transmit and receive an RF signal to and from blood vessel 10 and tissue 12) is connected to modulator 52 which is in turn connected to an RF signal generator 54 and is arranged to impose an RF signal at a selected frequency and at selected times upon vessel 10 and tissue 12. RF antenna 50 is also connected via amplifier 57 to demodulator 58, which is arranged to demodulate received signals (from vessel 10 and tissue 12) into quadrature real and imaginary components (indicated by the doubling of line 60).

Computer processor 70 is connected via I/O interface 71 to $G_x$, $G_y$, and $G_z$, drivers 42, 44, 36, to control the magnitude and timing of the linear gradient pulses imposed along the three axes upon vessel 10 and tissue 12, and to signal generator 54 to control the frequency, magnitude, and timing of the RF pulses.

Processor 70 is also connected via I/O interface 71 to demodulator 58 to receive the real and imaginary components of the demodulated received RF signal.

Processor 70 is further connected to a memory 72 (which stores software to control the operation of the system and data representing the received RF signals), to a CRT 74 (which displays images representing the received RF signal, as well as information needed by the operator to control the system), and to a keyboard 76 (by which the operator can enter data and information to control the entire operation of the system). A camera 75 attached to CRT 74 takes photographs of the displayed images.

Referring to FIG. 3, processor 70 includes $G_z$ pulse magnitude and timing control 90 which is connected to trigger $G_z$ driver 36 to apply selected levels of gradient at selected times. Likewise $G_x$ and $G_y$ pulse magnitude and timing controls 92, 94 are connected to trigger respectively $G_x$ and $G_y$ drivers 42, 44.

Similarly RF signal generator frequency, magnitude, and timing control 96 is connected to trigger RF signal generator 54 to provide an RF pulse having a selected frequency and magnitude, at selected times.

Controls 90, 92, 94, 96 are all connected to a sequencer 100 which provides the necessary specific magnitude, timing, and frequency parameters at the proper times for a given NMR field pulse sequence.

Sequencer 100 is connected to a user-entered parameter processor 102 which receives parameters from the keyboard and converts them to a form usable by sequencer 100.

Sequencer 100 is also connected to control an A-to-D converter 104 which is in turn connected to demodulator 58 to digitize the real and imaginary components of the received RF signal. A sampler 106 is connected to the converter 104 to sample the digitized signal components and to memory 72 to store the samples for later processing.

A Fourier transform element 108 is connected to memory 72 for performing a complex two-dimensional Fourier transform on a family of received signal samples to produce real and imaginary components of a two-dimensional array of data in the frequency domain. The parameters in accordance with which the Fourier transform is performed are received from processor 102 based on user entered information.

A display controller 110 is connected to Fourier transform element 108 to organize and process the frequency domain data into image information for delivery to CRT 74, again in accordance with parameters received from processor 102 as provided by the user.

Sequencer 100 is also connected to gating circuitry 112 which provides signals enabling the sequencer to synchronize successive pulse sequences to occur at the same point in successive heart beats.

The invention can be implemented by appropriately connecting and configuring available hardware and by specifying operating parameters for available related software, in accordance with the foregoing and following description (for example, NMR imaging hardware and software available from Technicare Corporation, Solon, Ohio, or similar systems available from other vendors).

OPERATION

Figure 4:
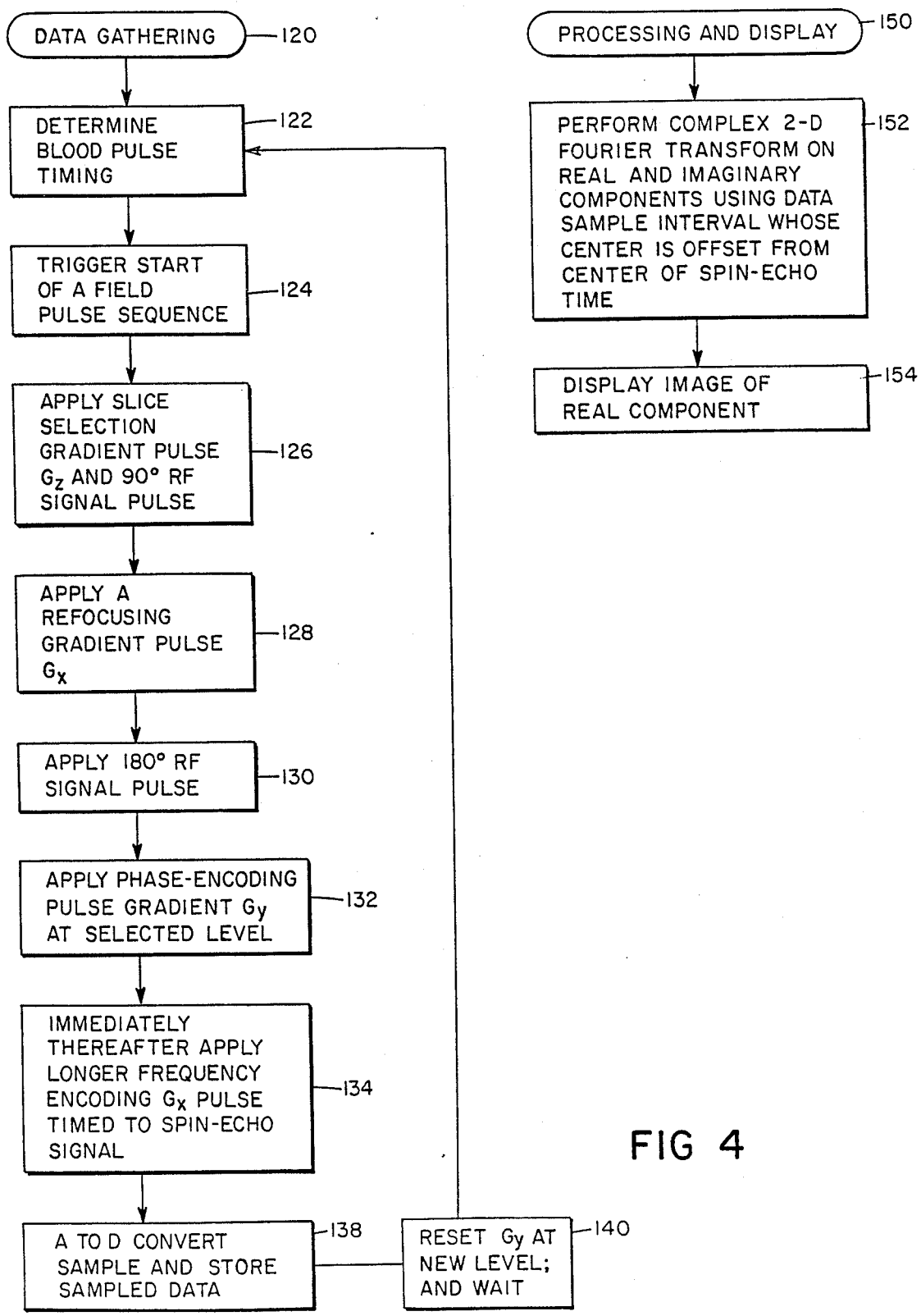
FIG. 4 is a flow chart of data gathering and processing and display steps.
Figure 5:
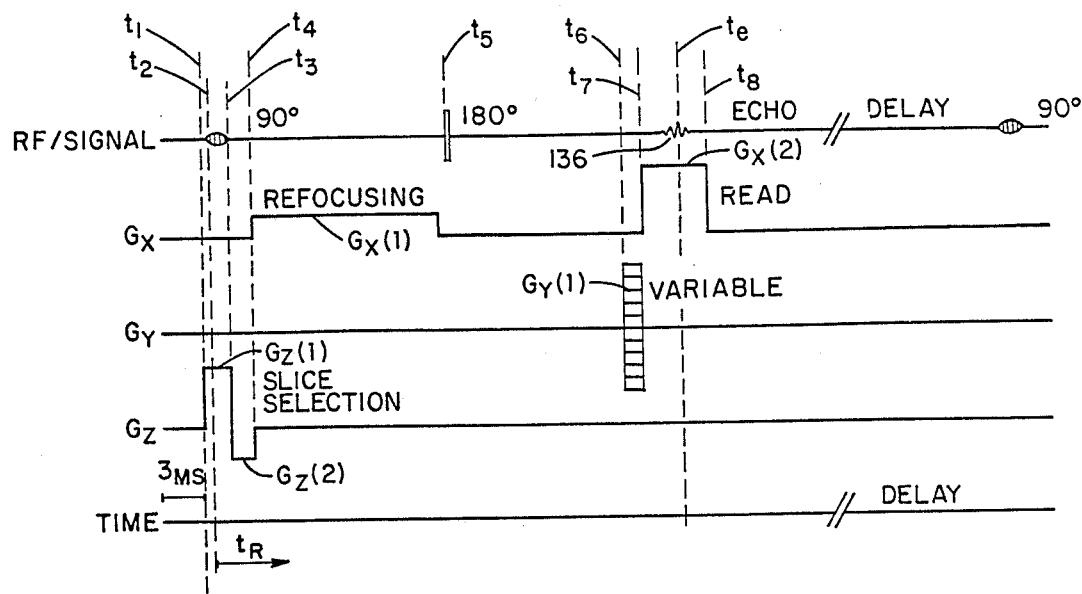
FIG. 5 is a timing chart (not to scale) of a pulse sequence for slice-selective imaging.

Referring to FIGS. 4, 5, in order to generate blood velocity profile images corresponding to planar slice 18 (FIG. 1), vessel 10 is oriented as nearly as possible to lie in the x-y plane with the predominant direction of its axis lying along the x-axis, and the system parameters are configured to perform two series of steps, one for data gathering and the other for processing and display. In the data gathering series (120), the blood pulse timing is first determined (122). At a preselected time ($t_1$) relative to the blood pulse a signal pulse sequence is begun (124) by applying a slice selective field gradient pulse $G_z(1)$ (126). While the slice selective gradient is being applied, a 90° RF pulse is applied during the period between times $t_2$ and $t_3$(126). The effect of the $G_z$ and RF pulses is to excite only those nuclei within planar slice 18, the slice of interest. During the period between times $t_3$ and $t_4$ a gradient $G_z(2)$ of opposite polarity to $G_z(1)$ is applied. At time $t_4$, a refocusing gradient pulse $G_x(1)$ is applied (128). At time $t_5$, a 180° RF signal pulse is applied (130) to flip the magnetization vector of the nuclei, causing their phases to tend to reconverge.

In the interval between times $t_6$ and $t_7$ a linear phase-encoding pulse gradient $G_y$ at a selected level (e.g., level $G_y(1)$ on FIG. 5) is applied (132) to encode the nuclei along the y-axis with different phases. Immediately thereafter and during the interval between times $t_7$ and $t_8$, a linear frequency-encoding gradient "read" pulse $G_x(2)$ is applied (134) which imparts different frequencies to different nuclei along the x-axis. Pulse $G_x(2)$ is timed to occur over an interval which spans the spin-echo signal 136, whose center point occurs at $t_e$.

The time durations of the $G_x$, $G_y$, and $G_z$ gradient pulses are shown only schematically in FIG. 5. Preferably pulse $G_y$ is about two to three times as long as pulse $G_z$, and pulse $G_x$ is about 5 to 20 times as long as pulse $G_y$. Thus for $G_z$ between 1 and 2 milliseconds, $G_y$ would be between 2 and 3 milliseconds, and $G_x$ between 10 and 20 milliseconds. It can be shown (as suggested in the Hahn article cited above) that the phase shift in a spin echo experiment depends on the square of the time duration of the gradient pulse. The contribution of the x-axis gradient pulse and hence of the velocity component along the x-axis is thus caused to dominate the total phase shift. For example, with $G_x$ lasting 10 times longer than $G_y$, the x-axis velocity will be weighted by a factor of 100 in the phase shift.

Referring again to FIGS. 4, 5, spin-echo signal 136 is sensed, A-to-D converted and sampled, and the samples (representing a time sequence of signal amplitude levels) are stored (138). That completes the data gathering steps for one time dependent set of signal samples. (The identical steps can be repeated several times with the results being averaged to improve the signal-to-noise ratio.)

A family of such signal sample sets is obtained by repeating the steps a number of times, each time using a different magnitude for the phase-encoding gradient pulse $G_y$. Thus, between iterations, the level of $G_y$ is reset and a delay period is allowed to pass (140) before the next iteration begins. The delay period can be selected to synchronize each iteration with the heart beat.

Once the family of signal sample sets are taken and stored, they are processed and displayed (150). A complex two-dimensional Fourier transformation is performed (152) to give spatially dependent real and imaginary components in the frequency domain for a two-dimensional array of pixels, and the real component array is displayed (154) as an image representative of the velocity profile of the blood over planar slice 18. In the image, the intensity represents the real part of the complex image datum at each pixel. The midpoint of the greyscale represents the zero value. Data with real parts greater than zero (corresponding to phase angles with positive cosines) give an image intensity value greater than the zero value. Data with negative real parts give image values less than the zero value.

Figure 6:
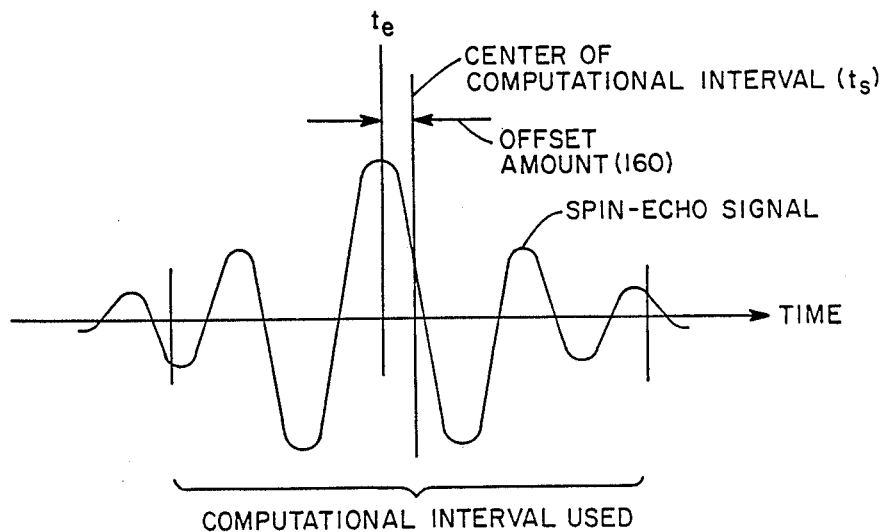
FIG. 6 is a graph of spin-echo signal data.

Referring to FIG. 6, in performing the Fourier transformation, the set of signal samples which are used for the computation span a time interval whose center time ($t_s$) is different by a small offset amount 160 from the center of the spin-echo signal ($t_e$). The effect of the offset in the Fourier transformation process is that the image data is multiplied by a phase factor that depends linearly on the frequency-encoded coordinate, x. For each sampling interval (e.g., 30 microseconds) within the offset amount there is produced 180° of total background phase variation across the image in the x direction. The result is a striping of the image which improves readability.

Information about the motion of the blood through vessel 10 during the course of each pulse sequence can be shown to be carried through to the Fourier transformed spatially dependent data in the form of apparent phase shifts, whose magnitudes depend on the velocities of the nuclei. The real component of the Fourier transformed data preserves this phase shift information, so that a display of the real component will show variations in the phase shift in a pattern which will reflect the velocity profile within vessel 10. By orienting the length of the blood vessel along the same axis (the x-axis) as the frequency encoding gradient pulse, and by making the frequency encoding gradient pulse longer than the phase encoding pulse, the resulting Fourier transformed image data is made more sensitive to velocity along the x-axis than along the y-axis. Offsetting the sample interval relative to the center of the spin-echo signal has the effect of adding a linearly increasing phase shift in the x-axis direction which produces a highly useful striping of the image as explained below.

Placing the phase-encoding pulse $G_y$ close in time to the frequency-encoding pulse $G_x$ reduces any error which might occur as a result of the nuclei changing position between the two pulses.

In one example, a velocity profile image was formed of water flowing through a 7/16" inside diameter tube. Flow was constant, gravity driven, and calibrated with a Mettler top-loading scale. The water was doped with $CuSO_4$ to have a relaxation constant $T_1$ of approximately 300 milliseconds at 20 megaherz. The tube was placed in the magnetic field with its axis aligned with the direction of the frequency-encoding gradient (i.e., along the x-axis). Because the flow was constant, rather than pulsatile, the pulse sequences were not gated to flow pulses, but were simply repeated every 300 milliseconds. The frequency encoding gradient strength was $6 \times 10^3$ Hz/cm. The resulting phase shift as a function of velocity of the nuclei can be calculated as 8.2 radians/cm/sec. The ratio depends on the pulse sequence which is preferably arranged so that the ratio will produce an image with striping which is useful for the flow velocities of interest. Ratios of at least 0.2 radians/cm/sec. appear to be useful. The magnet was a 1.44 T. (61.5 MHz) 8 cm superconducting magnet (fabricated by Technicare, Solon, Ohio).

Figure 7:
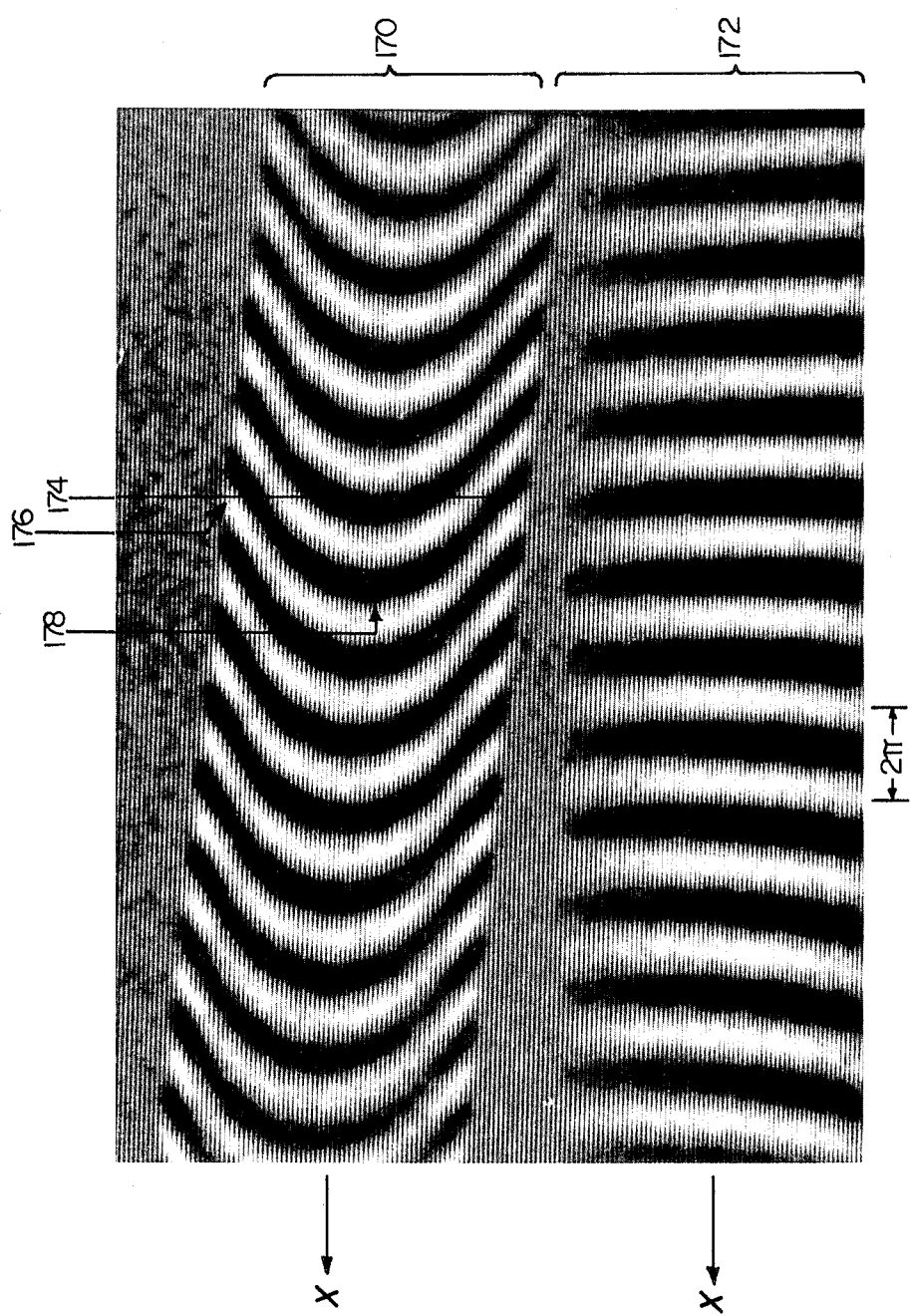
FIG. 7 is an image of two parallel tubes respectively containing static fluid and moving fluid.

Referring to FIG. 7, the upper half 170 is a display of the real component of the Fourier transformed data resulting from fluid flow in the tube, while the lower half 172 resulted from an identical tube with the fluid not flowing.

The lower half image 172 shows a stripe pattern with the stripes orthogonal to the x-axis. The stripes represent a background phase which increases linearly with distances along the x-axis. Each black or white stripe represents a background phase shift of 180° ($\pi$ radians). In upper half image 170, the phase shift due to the motion of the fluid is superimposed over the linear background phase shift. Thus the image gives an easily seen representation that the velocity along the central axis of the tube is higher than along the wall (because at the central axis the phase shift per unit length along the x-axis is greater). Further, because each stripe represents 180° of phase shift, it is possible to measure the difference between the phases at the wall and at the central axis at one position (174) along the x-axis by counting the number of stripes which must be traversed along the central x-axis in order to reach the stripe which begins at line 174 at the wall of the tube. Here there are 3 stripes between points 176, 178, which amounts to a $3\pi$ radians phase shift which translates to a maximum flow velocity of 1.2 cm/sec ($3\pi$ radians=1.2 cm/sec) or an average flow velocity of 8.2 radians/cm/sec 0.6 cm/sec, which is within 15% of the mechanically calibrated average velocity.

The display format enables direct inference from striping of data phase with a precision of ±90°, which is acceptable if small compared with typical phase shifts being studied. By using pulse sequences whose magnitude and duration produce relatively high phase shift/velocity ratios, phase shifts of many times 360° can be obtained.

Figure 8A:
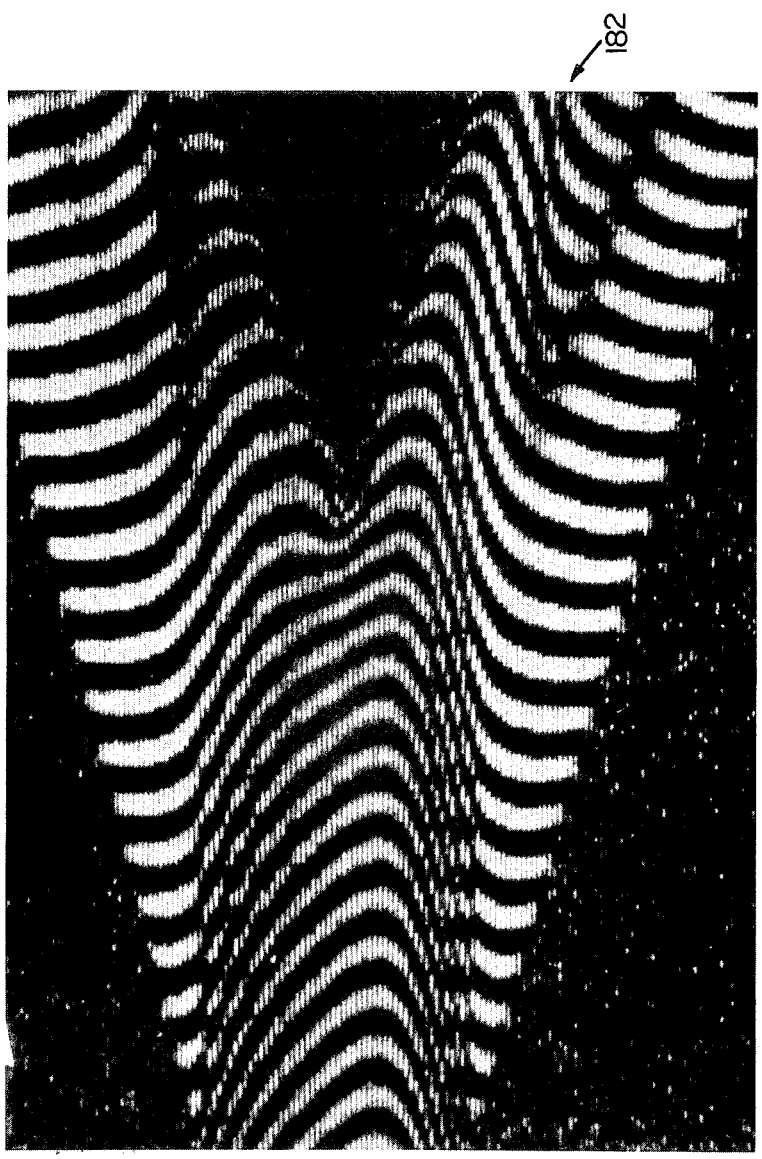
FIG. 8 shows images of bifurcating tubes respectively containing moving fluid and static fluid, and recombining tubes containing moving fluid.
Figure 8B:
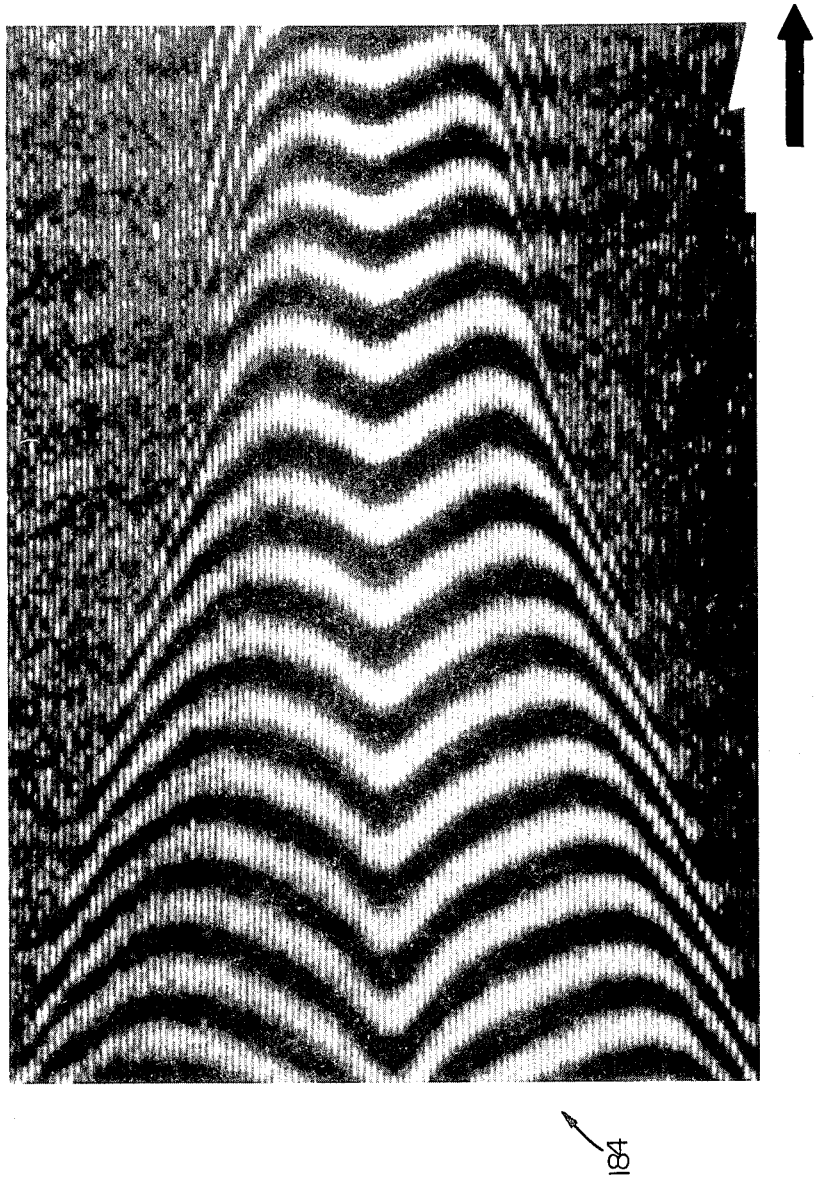
Figure 8C:
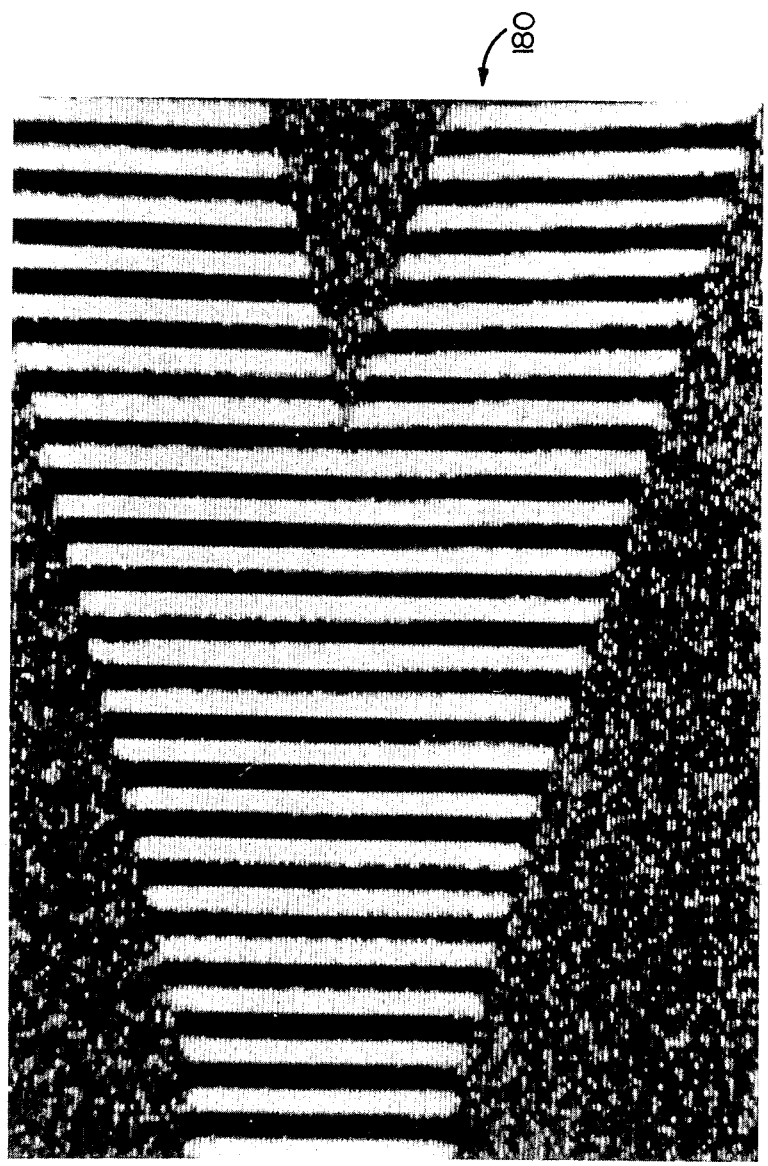

Referring to FIG. 8, in another example, the phase image produced by non-moving fluid in a bifurcating tube is shown in the lower left (180), and produces a set of parallel stripes representing the background phase offset. When the fluid is moving (182), the stripe pattern is shifted to reflect the velocity profile of the fluid. An image of fluid moving through tubes which recombine is shown in the upper right of FIG. 8 (184). In FIG. 8, the tube diameter is ⅛", and flow rate is 100 cc/min. The maximum phase shift discernible on the images is $10\pi$ radians corresponding to a maximum velocity of 3.83 cm/sec. The maximum expect velocity (based on fluid mechanics) is 4.0 cm/sec., within about 2% of the measured figure.

Figure 9A:
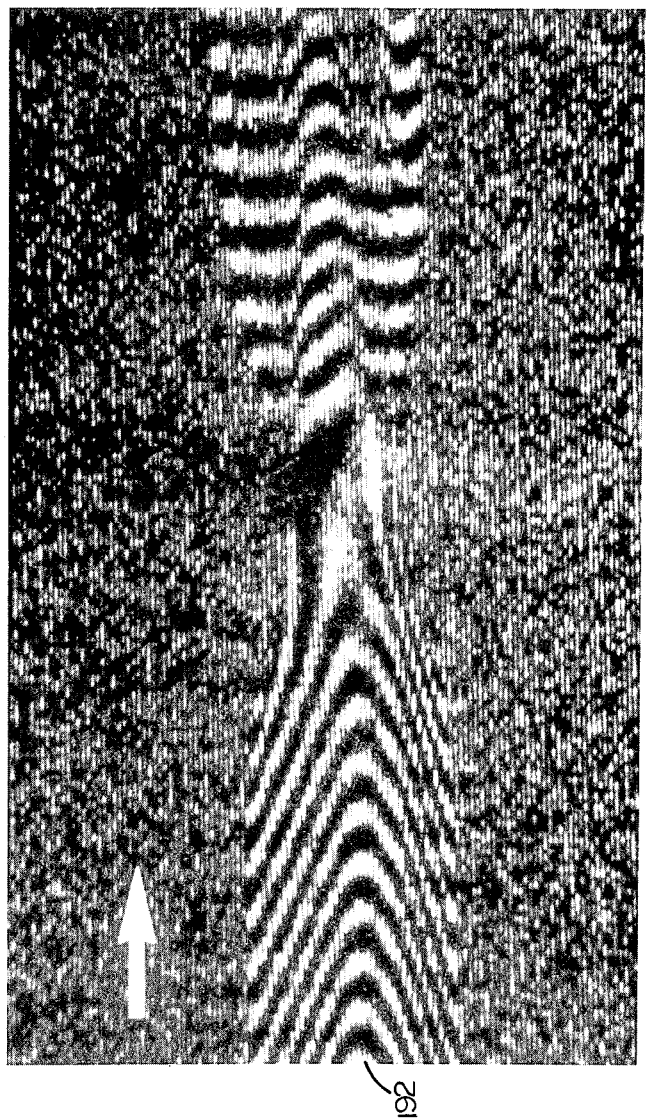
FIG. 9 shows images of constricted tubes respectively containing moving fluid and static fluid.
Figure 9B:
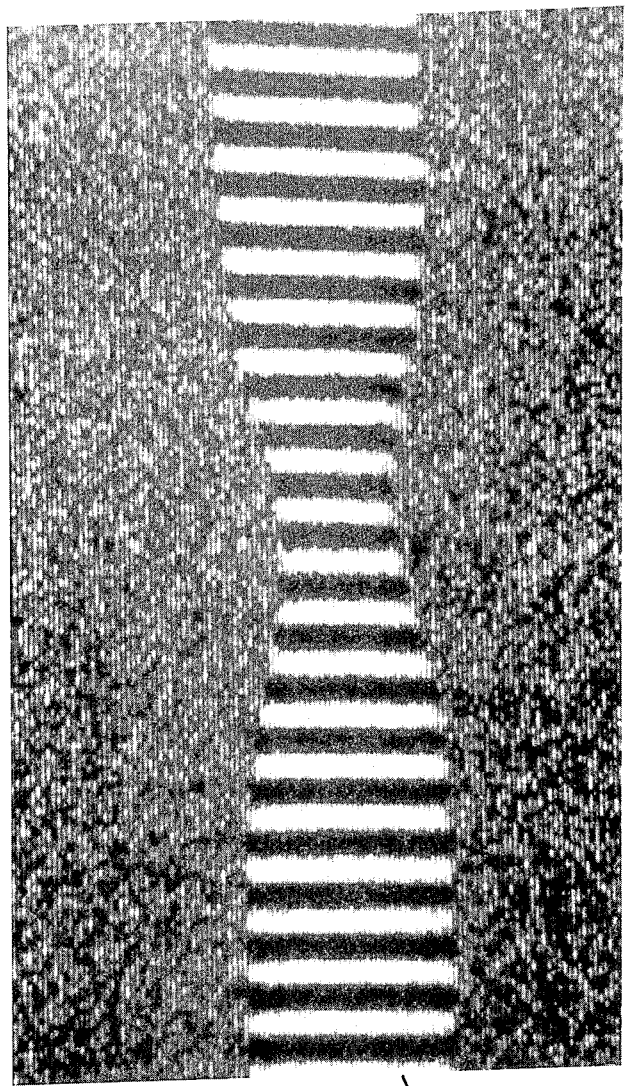

Referring to FIG. 9 in another example, images of a 3/16" inside diameter tube with a 3/32 inch stenosis (constriction) are shown for non-moving (190) and moving fluid (192).

In the images of moving fluid, velocity is inferred from the displacement of the stripes left or right, with the slopes of the stripes representing changes in flow velocity. Phase stripes which show forward concavity thus do not imply retrograde flow, but rather the existence of higher shear rates near the central axis compared with the tube wall (as in laminar flow).

Pixels where the phase becomes indistinct correspond to points where the velocity gradient is high enough that different velocity values coexist within one pixel. Interference of the resulting phases causes loss of signal, an effect which can be reduced by increasing the spatial resolution. Alternately, as explained below, such interference can be exploited to produce high contrast projection images of blood flow.

Introduction of a background phase offset into the imaging phase enhances the readability of phase shifts for four reasons. First, phase shifts can be calculated in two ways: stripe count or X displacement. Accuracy and precision are improved by this redundancy. Second, two-dimensional Fourier transform images have better resolution in X than in Y which gives the X displacement method the advantage. Third, background offset exposes any imperfections in the background phase, enabling correction by the reader. Fourth, in consequence of the first three advantages, phase offset enables the implementation of pulse sequences with higher characteristic velocity/phase shift ratios, reducing the importance of any residual phase ambiguity.

The system can also be used to generate so-called projection images, in which data from a number of stacked planar slices are effectively accumulated into one array. For example, a projection image of FIG. 1 would represent not only slice 18 but slices above and below it along the z-axis.

Figure 10:
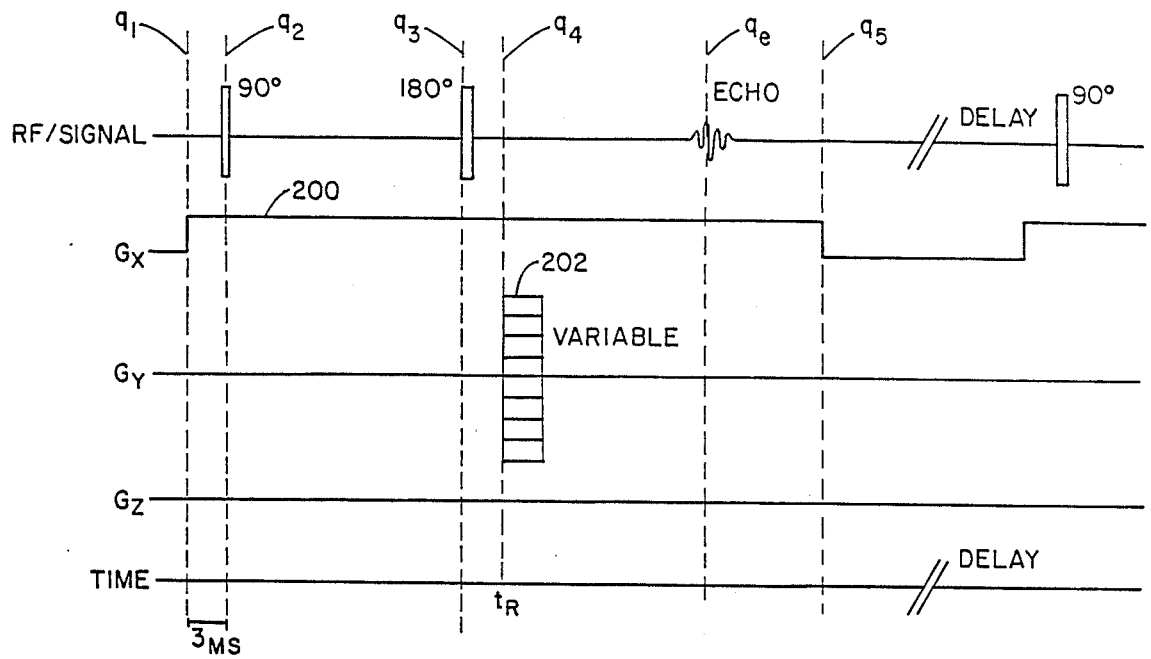
FIG. 10 is a timing chart of a pulse sequence for projection imaging.

Referring to FIG. 10, the pulse sequence for taking a set of samples for a projection image begins at time $q_1$ with the start of a long frequency-encoding gradient pulse 200. No slice-selective gradient pulse $G_z$ is used since the image is not meant to be slice-selective. At time $q_2$ (while the $G_x$ pulse continues) a 90° RF pulse is imposed, followed by a 180° pulse at time $q_3$, and a phase encoding gradient pulse 202 beginning at time $q_4$. The spin-echo signal is centered at time $q_e$. Gradient pulse 200 ends at time $q_5$, after which a delay occurs before the next pulse sequence begins. Thus, the projection images are obtained without either slice selection or z-axis encoding.

The Fourier transformation of the sets of data samples is performed without imposing the background phase offset used for the slice-selective images. Instead, the data component 90° away from the phase of the stationary nuclei in the object being imaged is the one used to form the image. This in effect suppresses the contribution of the stationary nuclei to the final image, while emphasizing the contribution of the moving nuclei. A greater than 90% reduction in stationary nuclei signal intensity has been achieved, permitting the imaging of flow velocities greater than 10 cm/sec with vessel diameter to total diameter ratios greater than 1/20.

Figure 11A:
FIG. 11 shows projection images of a bifurcating tube which contains moving fluid and is immersed in a container of water.
Figure 11B:
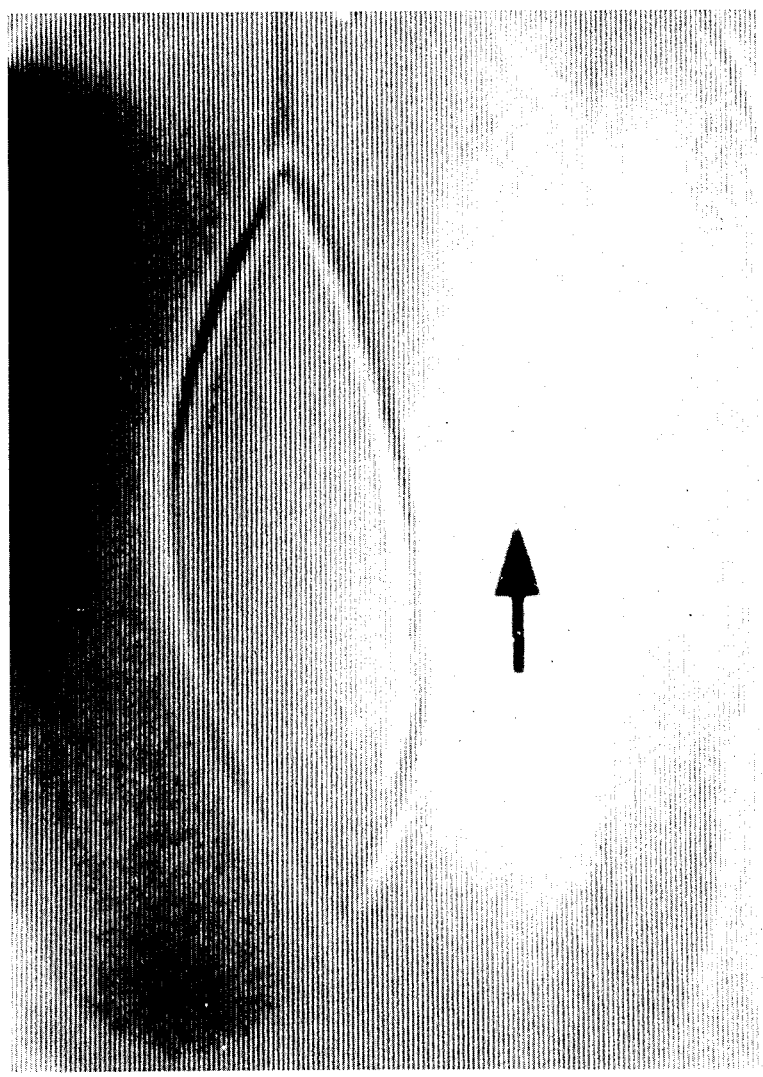

Referring to FIG. 11, the upper portion 210 shows a projection image of a bifurcating and recombining tube through which fluid is flowing at 300 cc/min. The ¼" inside diameter tubing lies within an 8"×10"×12" cavity of stationary water. The measured maximum phase shift is $5\pi$ radians which implies a maximum velocity of $V_{max}$, =6.44 cm/sec. The expected value of $V_{max}$ is 12.0 cm/sec, illustrating that projection imaging underestimates velocities. In this case, however, it would be more reasonable to expect projection images to represent the average velocity, $V_{avg}$, rather than $V_{max}$ since the entire tube diameter contributes to the observed phase shift. In this experiment $V_{avg}$=6.0 cm/sec, close to the observed velocity value.

Figure 12:
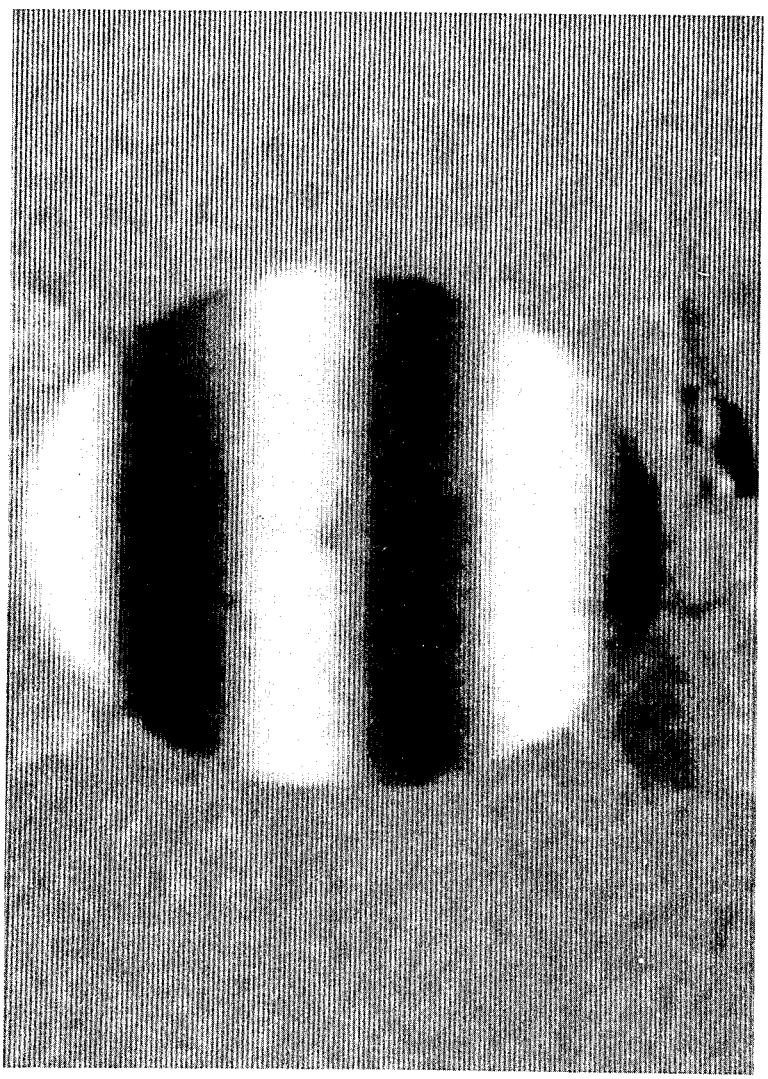
FIG. 12 shows a projection image of a rotating disk.

FIG. 12 is another example of projection imaging, this time of a rotating disc, with the axis of rotation aligned with the z-axis. The disc is composed of water-saturated towels inside a plastic container 20 cm in diameter and 1.5 cm thick. The disk is rotating at 30 rpm corresponding to a maximum tangential velocity of $10\pi$ cm/sec. A rigid body rotating in the x-y plane at frequency w has the property that at any point (x,y), the velocity $V(x,y)=2\pi/w/(y,-x)$. Therefore the x velocity component is proportional to y, and points of equal phase shift lie on horizontal lines (constant y) because they sustain equal x velocities. The pulse sequence was repeated every 300 msec, $t_e$=10.0 msec, the frequency encoding gradient was $G_x=3\times10^3$ Hz/cm and the calculated ratio of phase to velocity was $P(t_e)/V_x$=0.28 radians/cm/sec.

At 30 cm/sec, this corresponds to a total phase shift of $3\pi$ radians which is in reasonable accord with the experiment. This demonstrates that high velocity can yield good signal intensity without spatial distortion.

Projection imaging is highly efficient, enabling three-dimensional volume to be surveyed in times characteristic of two-dimensional imaging experiments.

In another technique for generating projection images, two distinct sets of data are accumulated, then subtracted to form a resulting image. The two data sets are derived in such a manner that, for static portions of tissue, the data are identical and cancel, while for moving portions (such as blood) the two data sets differ. One data set is taken during systole, the other during diastole. In the resulting image the blood, and implicitly the vessels in which it flows, are seen clearly, while the static tissue is suppressed.

Figure 13:
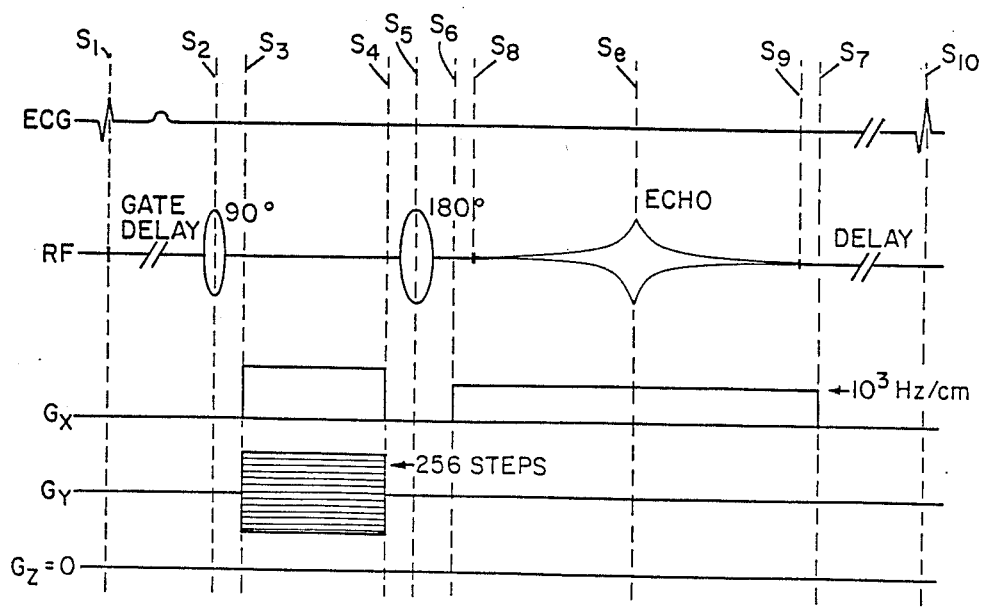
FIG. 13 is a timing chart (not to scale) of a pulse sequence for subtractive projective imaging.

Referring to FIG. 13, the pulse sequences (a two-dimensional Fourier transform sequence) begins at a time $s_1$ when the QRS complex occurs in the electrocardiogram (ECG). At time $s_2$, after an appropriate gate delay whose duration is based (in a manner described below) on whether the data is being taken for systole or diastole, a 90° RF pulse is imposed. Thereafter, in the interval between $s_3$ and $s_4$, a compensating gradient pulse $G_x$ is applied simultaneously with a phase encoding pulse $G_y$ at a selected one of 256 different levels. Next, at time $s_5$ (i.e., 4.5 milliseconds after $s_2$ or half the 9 millisecond interval between $s_2$ and the echo signal—$s_e$) a 180° RF pulse is imposed. The spin echo signal is spanned by a frequency encoding readout gradient pulse $G_x$ (equivalent to 1,000 Hz/cm) in the interval between $S_6$ and $S_7$.

The spin echo signal is centered at time $s_e$. The readout period occurs between $s_8$ and $s_9$.

The combined effect of the compensating $G_x$ pulse and the readout $G_x$ pulse, which straddle the 180° RF pulse is to cause no net phase component to be imparted to static protons but to cause a net phase component to be imparted to each moving proton. The net component depends on the fact that because the proton moves to a new x position in the time between the occurrences of the two $G_x$ pulses, it is subjected to different magnitudes of phase shifting by the two $G_x$ pulses; those magnitudes (which in static protons would be equal and therefore cancel) do not cancel.

Following the readout period with respect to one pulse sequence, a new pulse sequence (using a different value for the $G_y$ gradient) is begun at time $S_{10}$ upon the occurrence of the next QRS complex. A succession of 256 pulse sequences one for each different value of $G_y$ is used with a gate delay appropriate to diastole to obtain a first data set. A second succession of 256 pulse sequences is used with a gate delay appropriate to systole to obtain a second data set. The pulse sequences used to obtain the two data sets are identical. Referring to FIG. 27, the respective gating delays for systole and diastole are both provided by gating circuitry 112 to a switch 113 that passes the appropriate delay to sequencer 100. Referring to FIG. 28, processor 70 performs a two-dimensional complex Fourier analysis (in element 108) of the resulting two arrays, producing two corresponding images of the same subject respectively gated to diastole and systole 109, 111. The images are subtracted from each other (in element 115) to obtain a clear resulting blood flow image of high contrast and high resolution in which the static tissue is suppressed. In practice, it has been found necessary to weight the two data sets before subtraction in order to maximize the cancellation of the static proton signals and hence the image contrast. The weighting has been done empirically by applying different weights to a background region of the data sets until the minimum background image intensity is obtained.

The pulse sequence of FIG. 13 is designed to generate velocity-dependent proton phase shifts in the blood of 1 cycle per meter per second. This is accomplished, in particular, by arranging the echo time (i.e., the interval between $s_2$ and $s_e$) to be no greater than 15 milliseconds, preferably no greater than 10 milliseconds. This value results in the relative preservation of the blood proton signal for diastolic flow velocities (which are, e.g., typically less than 0.1 meters per second) because the velocity imposed phase shifts are quite small and the blood proton phases reinforce each other in the projected image. Conversely, the value of 1 cycle per meter per second produces a relative loss of the blood proton signal for systolic flow velocities (which are typically between 0.5 and 1.5 meter per second) because the velocity imposed phase shifts are large enough to cause a randomization of and hence cancellation of phases in the projection image. When the systole and diastole images are subtracted, the static tissue phases (which are identical in the two images) cancel while the blood phase in diastole remains highly visible as an indicator of blood flow.

Figure 14:
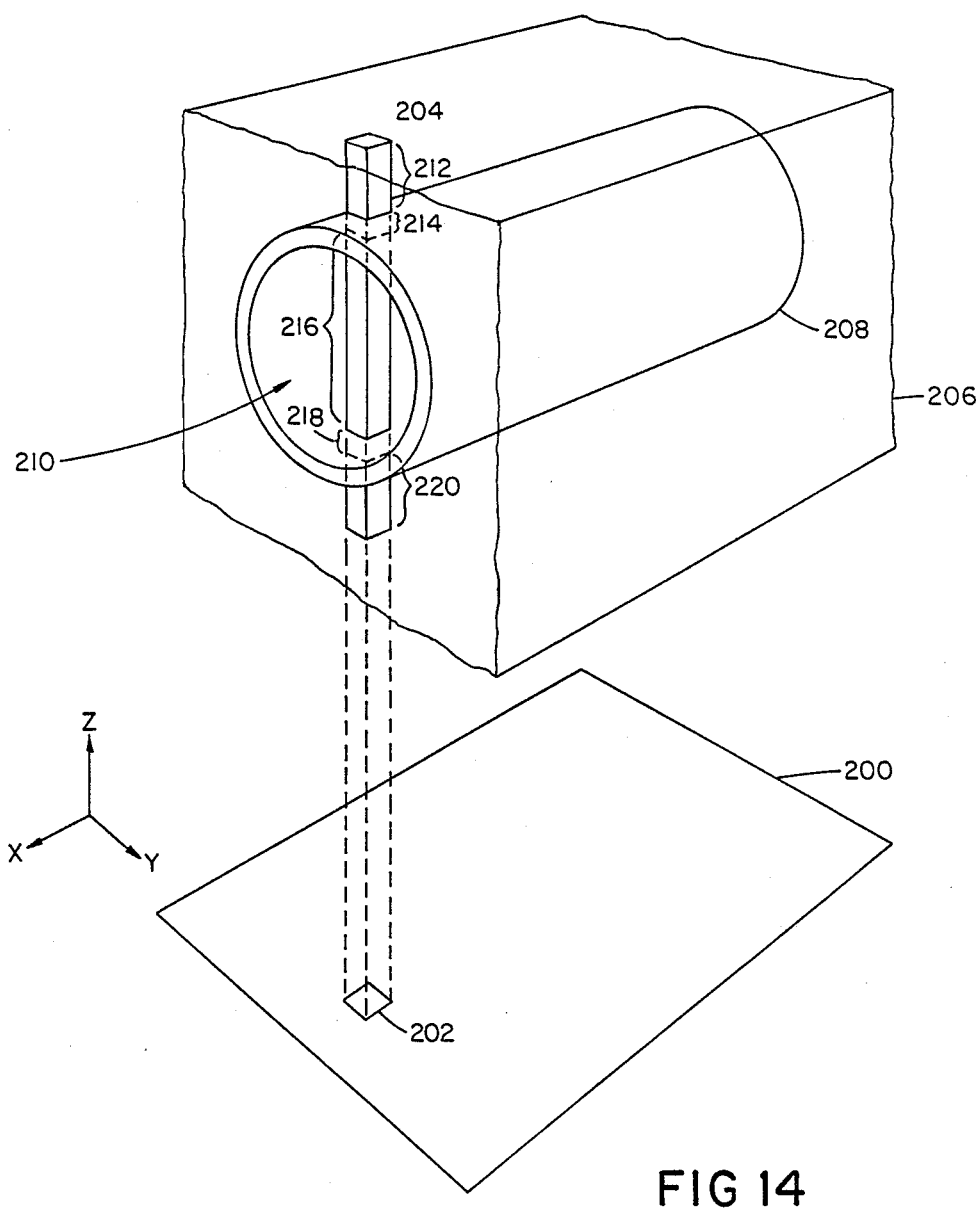
FIG. 14 is an isometric diagram of projective imaging.

Referring to FIG. 14, each projected image lies in an x-y plane 200 which includes a grid of 256 by 256 pixels (e.g., pixel 202, shown out of scale) in an area of 50 cm by 50 cm. Each pixel represents a projection of the proton signal from all protons in a voxel (volume element) 204 located at the same x and y coordinates as the resulting pixel 202 but spanning all z coordinate values in a sample that includes tissue 206, an artery 208, and moving blood 210 within the artery. Voxel 204 thus includes portions 212, 214, 216, 218, 220, that lie respectively in tissue, vessel, blood, vessel, and tissue.

Referring to FIG. 15, in each projective pixel 202, the resulting proton signal 230 has two constituents: a larger coherent part originating in the stationary background material 212, 214, 218, 220, and a smaller part originating in the blood protons 216 whose coherence depends on the flow velocity. At diastolic flow velocities the imaging pulse sequence produces phase shifts smaller than 0.1 cycle. In that case, the blood proton signal behaves coherently (as represented by the phase arrows in section 216 of FIG. 15, which point in generally the same direction) and adds to the background signal to form an additive resulting proton signal 230.

Referring to FIG. 16, in systole, peak velocities generate phase shifts of 0.5 to 1.5 cycles in moving blood protons 216. Each voxel 204, however, intersects the blood in vessel 208 along a chord of points (section 216 in FIG. 16) and so all velocities between zero and the maximum are sampled by partial volume averaging. This range of velocities yields a blood signal which behaves incoherently (as represented by the randomly directed phase arrows in segment 216 of FIG. 16) and makes little or no contribution to the net proton signal 232 for the pixel 202. Systole signal 232 is thus considerably smaller than diastole signal 230 (FIG. 15).

This subtractive projective imaging technique is performed in a 0.6 T (25 MHz, proton) superconducting imaging system (Technicare Corporation, Solon, Ohio). The brief duration of the data acquisition window (6 msec between $S_8$ and $S_9$ in FIG. 13) requires a comparatively large readout gradient $G_x$ of 0.25 Gauss per centimeter (corresponding to 1 kHz per centimeter, proton) and the use of a correspondingly broadband time-domain signal filter (50 kHz). To produce the two images for diastole and systole, data acquisition times for both data sets average 8 minutes (512 cardiac cycles in subjects with a normal pulse).

Artifacts caused by patient movement between the two data sets could be reduced by interleaving the systole and diastole pulse sequences, but the time between successive pulse sequences would have to be increased to accommodate the time required to switch the gating, thus increasing the aggregate time required for data acquisition. Respiratory artifacts could be removed by timing the pulse sequences to occur at the same times relative to the respiration cycles.

Figure 17:
Figure 18:
Figure 19:
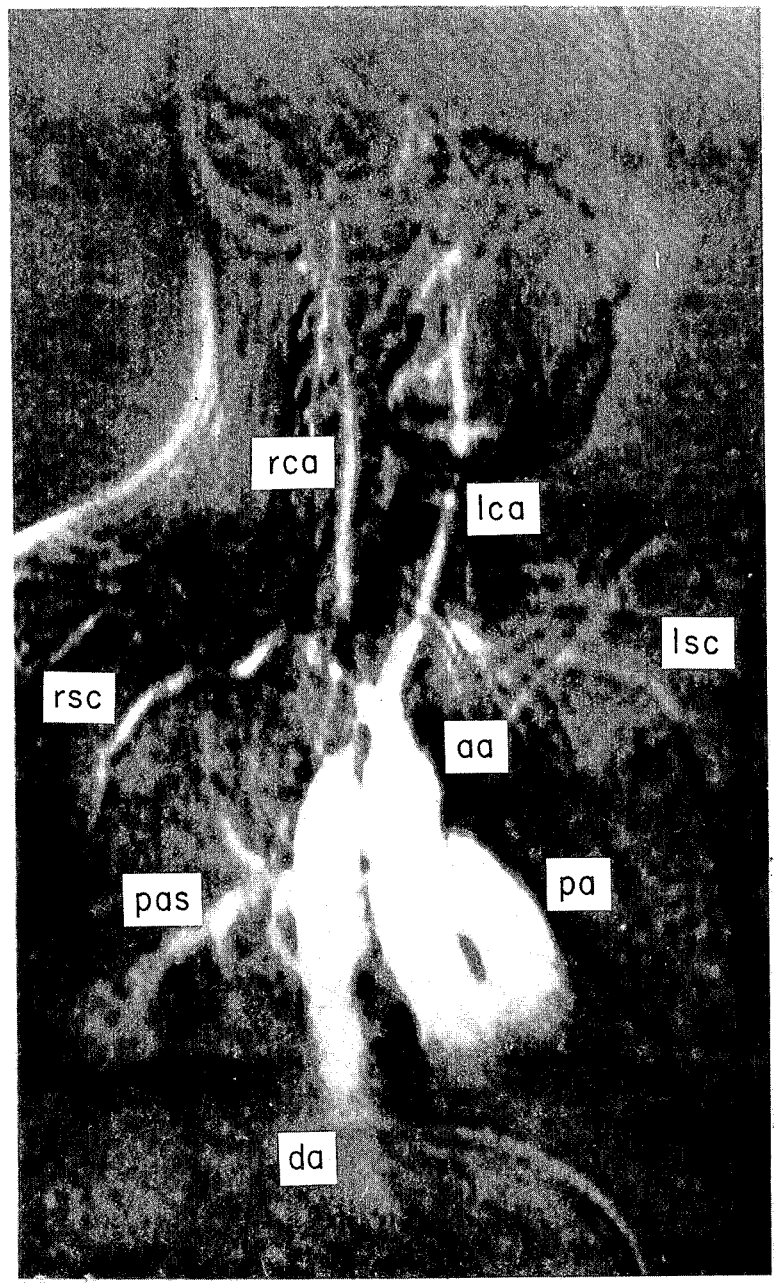
Figure 20:
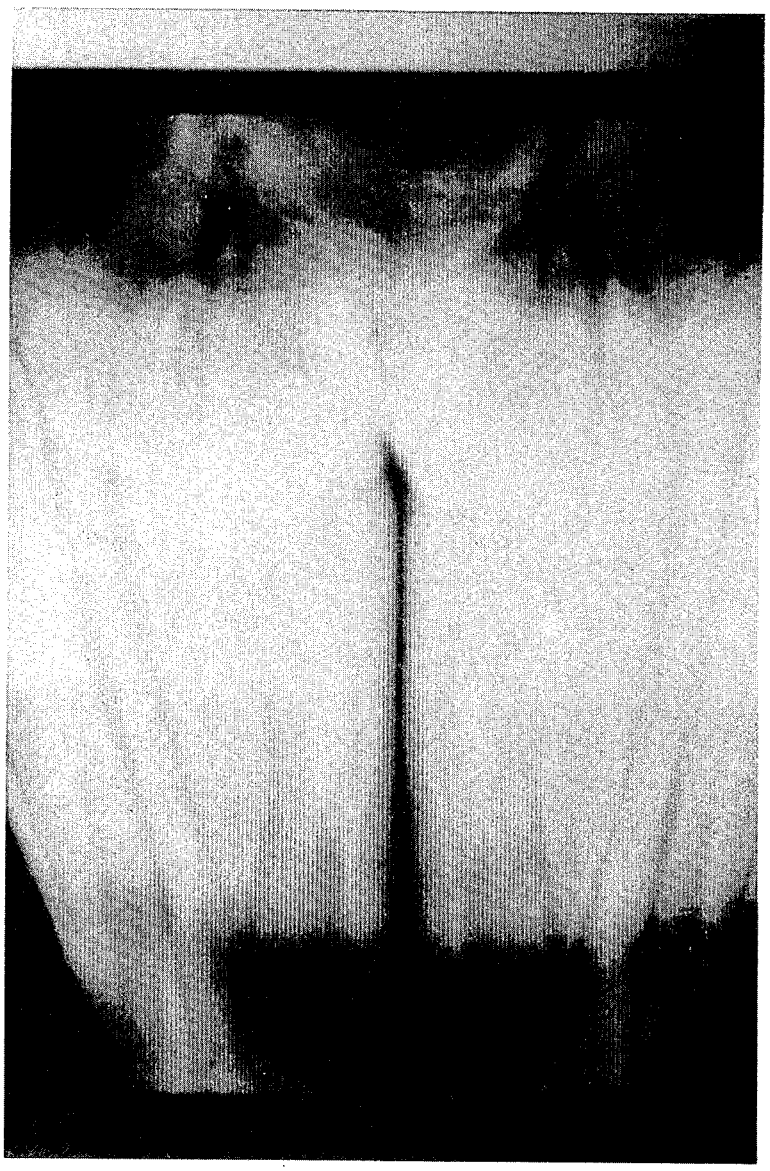
Figure 21:
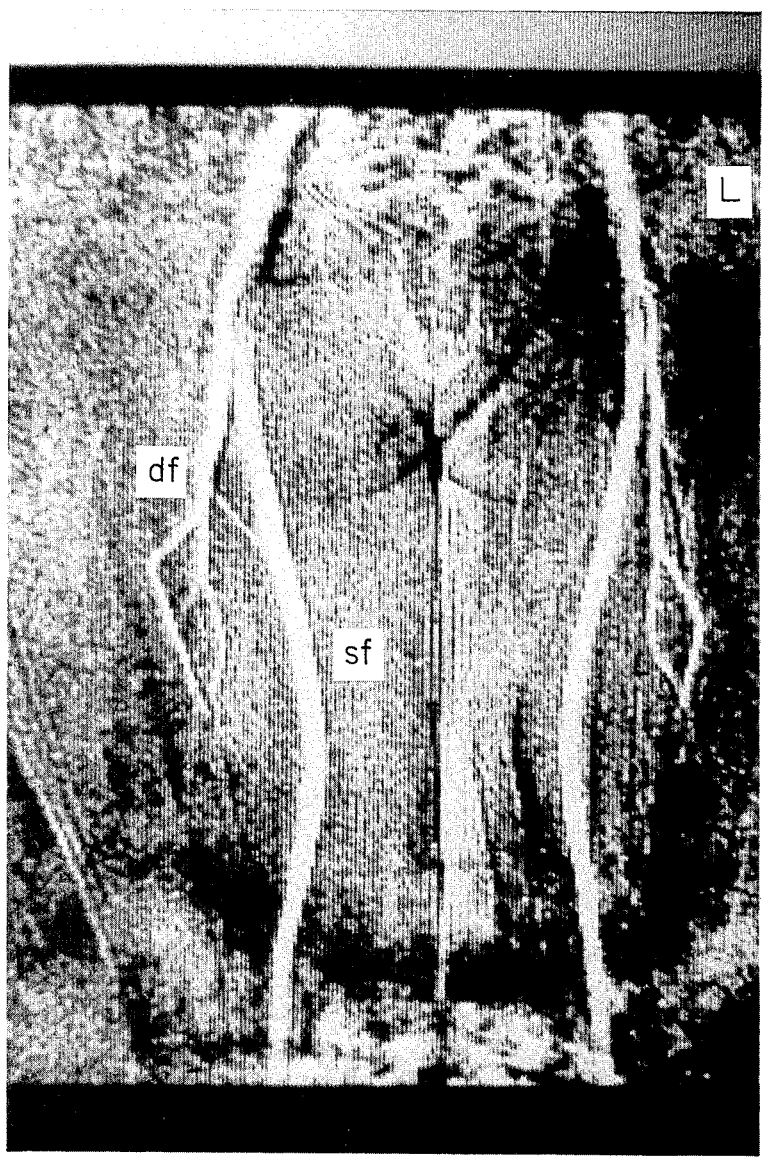
Figure 22:
Figure 23:
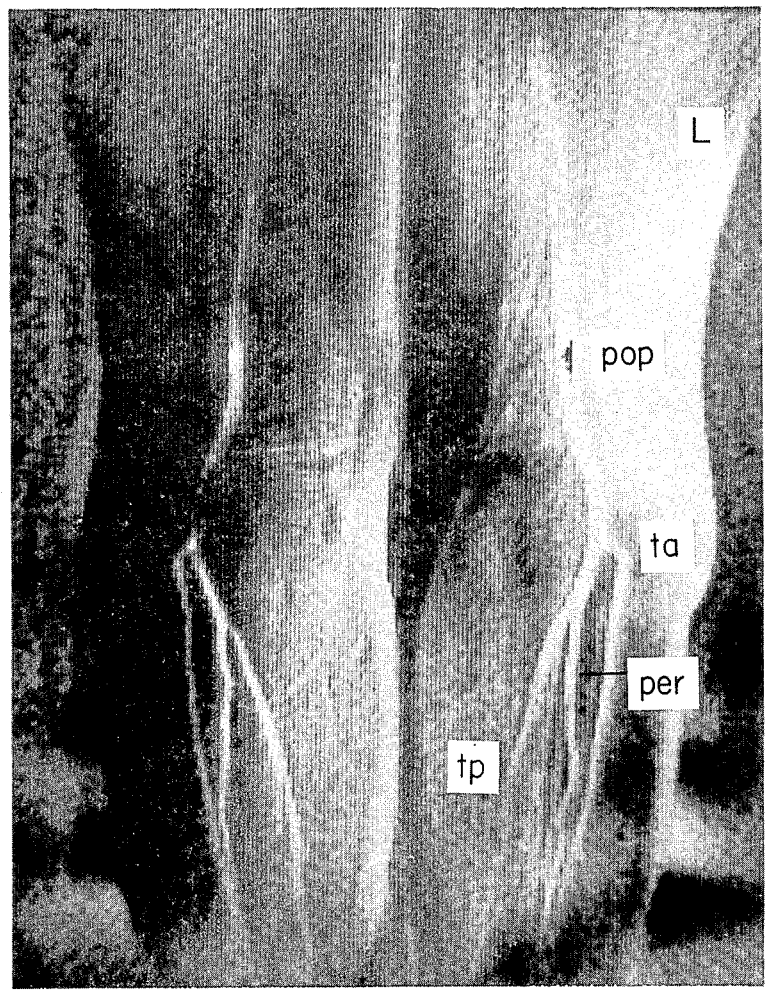

For example, FIGS. 17, 18, and 19 show respectively the diastolic, systolic, and resulting subtraction flow images of a human chest in a 45° right oblique projection in which the x coordinate (FIG. 14) appears vertically. The diastolic and systolic gate delays ($S_1$ to $S_2$ in FIG. 13) were respectively 10 and 150 milliseconds. Blood vessels seen in the flow image (FIG. 19) are labeled aa (ascending aorta), da (descending aorta), pa (pulmonary artery), pas (right pulmonary segmental branches), rca and lca (right and left carotid arteries), rsc and lsc (right and left subclavian arteries).

In another example, FIGS. 20, 21, 22, 23 show systolic (FIGS. 20, 22) and resulting flow images (FIGS. 21, 23) of thighs (FIGS. 20, 21) and knees (FIGS. 22, 23) of a human subject, projective to the coronal plane. The x coordinate is vertical. Diastolic gate delays of 10 msec were used for both knees and thighs; systolic delays of 250 and 300 msec were used at the thighs and knees respectively in this individual (height 180 cm). Arrows mark the superficial (sf) and deep (df) femoral arteries of the thigh and the popliteal (pop), anterior tibial (ta), posterior tibial (tp), and peroneal (per) of the knee and calf.

In another example, FIGS. 24, 25, 26 show x-ray (FIG. 24) and NMR systolic and flow (FIGS. 25, 26) images of atherosclerotic occlusions of the superficial femoral arteries, using gate delays of 10 (diastolic) and 300 (systolic) milliseconds. Arterial segments are marked as for FIGS. 17, 18, 19. Proximal and distal points of occluded segments are marked "0. prox" and "0. dist" (FIG. 24). The appearance of the popliteal arteries reconstituted by collateral flow images implies they are pulsatile (as was confirmed by Doppler ultrasound examination). The poor appearance of the right proximal superficial femoral artery is consistent with angiographically proven poor runoff in this vessel.

In these examples, one image parameter was tailored for each application: the systolic gate delay. Apart from individuals with ventricular dysrhythmias, the QRS complex itself coincides with arterial diastole so the diastole gating delay is always set at 10 milliseconds regardless of the location of the artery within the body. However, the arrival time of peak systolic flow is variable. In normal individuals arrival times increase with distance from the heart. Disease processes may either retard the pulse wave (e.g., aneurysm, occlusion) or accelerate it (e.g., nonocclusive atherosclerosis). The systolic gate delay was selected empirically in each case by performing between 1 and 4 brief (1 minute) low resolution (64×256 pixels) localization images. Typically the gate delay is between 100 and 300 milliseconds. Best results were obtained by exploring the likely range of gate delays in 50 msec increments.

Several factors will affect the contrast of the subtraction image, including the following. First, because the fraction of velocity which produces phase shifts (and hence contrast) varies as the cosine of the angle between the direction of blood flow and the x axis, vessels oriented at large angles to the x axis may be unobserved in the flow image due to an undiminished systolic signal. Two resulting flow images could be acquired, separated by a 90° rotation in the x-y plane. Each vessel will have a satisfactory orientation in at least one of these images. Second, flow contrast may be undercut by substantial diastolic flow velocities (greater than 0.1 meter per second) which reduce the diastolic blood signal. Doppler ultrasound data have shown that such diastolic flows occur at certain anatomic locations, notably in the arterial supplies of the brain and the visceral organs. Maximum contrast could be recouped by a diastolic acquisition with reduced phase shift. Third, a portion of the arterial blood protons are replaced during each interpulse interval (between $s_7$ and $s_{10}$ in FIG. 13) by unsaturated protons formerly outside the RF coil (proton refreshment). The saturated proton signal is less intense than the unsaturated proton signal by a factor $[1-\exp(s_7 - s_{10})]/T1_{blood}$, (where T1 denotes the longitudinal relaxation time). Affected arterial segments will have proportionally enhanced intensity in the flow image. Whether gating is systolic or diastolic, the interval between successive pulse sequences represents one cardiac cycle. Therefore, the physical locations in the vessel that are subject to proton replacement are well-defined. Image subtraction will subtract saturated protons in one data set from saturated protons in the other data set, and will likewise subtract unsaturated from unsaturated. Relative to image subtraction, proton refreshment thus resembles a static variable such as proton density more than a dynamic variable such as phase contrast.

Vascular imaging in the projective format efficient. Neither tomography nor existing 3-dimensional imaging techniques can present such detailed anatomy from such large territories in so compact and accessible a form. Projective imaging also yields purely technical benefits. Magnetic resonance imaging times grow exponentially with the dimensionality of the experiment. Though projective images are sensitive throughout a 3-dimensional volume, their data acquisition and processing requirements are those of 2-dimensional imaging. A related economy of this method is its reliance on completely conventional imaging pulse sequences and reconstruction. From a clinical standpoint, the non-invasiveness of this method may allow its application outside the compass of current indications for angiography. An example might be the periodic assessment of arterial bypass grafts. Pulsatility, the ultimate source of contrast, tells something more specific about functional capability than simple patency.

Other embodiments are within the following claims. Veins in which blood flow is pulsatile (or any vessel containing pulsatile flow of a fluid) can also be imaged.

I claim:

1. Nuclear magnetic resonance apparatus for forming an image representative of fluid flow in a vessel situated within a matrix, said fluid flowing with a first velocity profile at a first time and with a second velocity profile, different from said first velocity profile, at a second time, comprising
   means for stimulating said fluid, vessel, and matrix to produce a magnetic resonance signal, including means for providing a magnetic field gradient,
   means for deriving data from said magnetic resonance signal,
   said means for stimulating including means for introducing into said data phase information indicative of said velocity profile of said fluid as of a given time, and for controlling the time variation of said magnetic gradient field to induce phase shifts in said data corresponding to velocity,
   means for extracting a data set representative of a projection image of said fluid, vessel, and matrix as of said given time,
   means for causing said apparatus to generate two said data sets corresponding to two projection images respectively as of said first and second times, and
   means to combine said data sets to form a resulting data set in which the signal is cancelled or not according to whether or not said velocity, and hence said phase shift, changed from said first time to said second time, and
   means for displaying said resulting data set as said image representative of said fluid flow in said vessel.

2. The apparatus of claim 1 wherein
   said means for stimulating further comprises means for imparting a sequence of RF and magnetic gradient pulses to said fluid, vessel, and matrix beginning at a predetermined time to produce said resonance signal, and
   said sequences used to generate said two data sets are identical.

3. The apparatus of claim 1 wherein
   said first velocity profile includes a first range of velocities, and said second velocity profile includes a second range of velocities higher than said first range, and
   said means for stimulating includes means for imparting to protons in said fluid with respect to said first velocity profile, phases that are within a predetermined angle of the phases imparted to protons in said vessel and matrix, and for imparting random phases to protons in said fluid with respect to said second velocity profile.

4. The apparatus of claim 1 wherein
   said means for stimulating imparts a sequence of RF and magnetic gradient pulses to said fluid, vessel, and matrix that generates a phase shift in protons in said fluid at a rate of $2\pi$ radians for a predetermined velocity level of said fluid that is higher than said first range of velocities and lower than said second range of velocities.

5. The apparatus of claim 4 wherein said fluid is blood, said first range of velocities comprises the velocities of blood flowing in diastole, and said second range of velocities comprises the velocities of blood flowing in systole.

6. The apparatus of claim 1 wherein said fluid is blood, said first time is diastole, said second time is systole, and said apparatus further comprises
   means for triggering said means for stimulating at said first time based on the occurrence of said diastole, or at said second time based on the occurrence of said systole.

7. The apparatus of claim 6 wherein said second time follows said diastole by a predetermined interval based on the location of said vessel relative to the heart.

8. The apparatus of claim 6 wherein said first time follows a QRS complex by 10 milliseconds.

9. The apparatus of claim 6 wherein said second time follows said QRS complex by between 100 and 300 milliseconds.

10. The apparatus of claim 2 wherein said sequence comprises a two-dimensional Fourier transform spin echo pulse sequence.

11. The apparatus of claim 10 wherein said spin-echo pulse sequence comprises 90° and 180° RF pulses, and a pair of magnetic gradient pulses along an axis of said vessel, said gradient pulses comprising a compensating pulse preceding said 180° RF pulse and a readout pulse following said 180° RF pulse, said two magnetic gradient pulses being of magnitudes and durations such that for static protons the phase shift imposed by one said gradient pulse is exactly canceled by the phase shift imposed by the other said gradient pulse.

12. The apparatus of claim 10 wherein a spin echo occurs no later than 15 milliseconds after said 90° RF pulse.

13. The apparatus of claim 1 wherein said fluid is blood.

14. The apparatus of claim 1 wherein said vessel is an artery.

15. The apparatus of claim 1 wherein said matrix is tissue.

16. The apparatus of claim 1 wherein said fluid flow is pulsatile.

17. The apparatus of claim 1 wherein said data produced from said resonance signal comprises Fourier transformed data.

18. A method for forming an image representative of fluid flow in a vessel situated within a matrix, said fluid flowing with a first velocity profile at a first time and with a second velocity profile, different from said first velocity profile, at a second time, comprising stimulating said fluid, vessel, and matrix to produce a magnetic resonance signal, including generating a magnetic field gradient, deriving data from said magnetic resonance signal, introducing into said data phase information indicative of said velocity profile of said fluid as of a given time controlling the time variation of said magnetic field gradient to induce phase shifts in said data corresponding to the velocity, extracting a data set representative of a projection image of said fluid, vessel, and matrix as of said given time, generating two said data sets corresponding to two projection images respectively as of said first and second times, and combining said data sets to form a resulting data set in which the signal is cancelled or not according to whether or not said velocity, and hence said phase shift, changed from said first time to said second time displaying said resulting data set as said image representative of said fluid flow in said vessel.

19. The apparatus of claim 1 wherein said fluid is blood and said phase shifts are cancelled with respect to venous vessels and stationary parts of said matrix.

* * * * *

UNITED STATES PATENT AND TRADEMARK OFFICE
CERTIFICATE OF CORRECTION

PATENT NO. : 4,752,734

DATED : June 21, 1988

INVENTOR(S) : Van J. Weeden

It is certified that error appears in the above-identified patent and that said Letters Patent is hereby corrected as shown below:

Column 3, line 61, "direction tends" should be
--direction 14 tends--.

Signed and Sealed this

Seventh Day of February, 1989

Attest:

DONALD J. QUIGG

*Attesting Officer*  *Commissioner of Patents and Trademarks*